United States Patent [19]

Weissman et al.

[11] Patent Number: 4,710,465

[45] Date of Patent: Dec. 1, 1987

[54] JUNCTION-FRAGMENT DNA PROBES AND PROBE CLUSTERS

[75] Inventors: Sherman M. Weissman, New Haven; Francis Collins, Cheshire, both of Conn.

[73] Assignee: Yale University, New Haven, Conn.

[21] Appl. No.: 601,916

[22] Filed: Apr. 19, 1984

[51] Int. Cl.$^4$ .................. C12Q 1/68; C12N 15/00
[52] U.S. Cl. .......................... 435/91; 435/5;
435/6; 435/172.3; 435/253; 935/10; 935/23;
935/26; 935/27; 935/31; 935/76; 935/78;
935/80; 935/81; 935/82; 436/501; 436/504;
436/811; 536/27
[58] Field of Search ..................... 536/27-29;
435/91, 172.1, 172.3, 6, 5, 7, 4, 188, 235, 253,
243, 849, 948; 436/501, 504, 518, 528, 804, 811;
935/9, 10, 19, 22-24, 26, 27, 31, 55, 56, 58, 76-82

[56] References Cited

U.S. PATENT DOCUMENTS

| 4,394,443 | 7/1983 | Weissmann et al. | 435/6 |
| 4,395,486 | 7/1983 | Wilson et al. | 436/504 |
| 4,528,266 | 7/1985 | Pieczenik | 435/6 |
| 4,530,901 | 7/1985 | Weissmann | 435/240 |

OTHER PUBLICATIONS

Dugaiczyk, A. et al., J. Molec. Biol., 96; 171-184 (1975).
Botstein, D. et al., Am J. Hum. Genet.; 32, 314-331 (1980).
Sood, A. K. et al., Proc. Natl. Acad. Sci., USA; 78, 616-620 (1-1981).
Lazar, E. et al., Nucleic Acids Research, 10; 1193-1201 (2-25-1982).
Shows, T. B. et al., Adv. Hum. Genet., 12; 341-352 (1982).
Das, H. K. et al., Proc. Natl. Acad. Sci., USA, 80; 1531-1535 (3-1983).
Carroll, M. C. et al., Nature; 307, 237-241 (1-1984).
Collins, F. S. et al., Proc. Natl. Acad. Sci., USA; 81, 6812-6816 (11-1984), (not prior art.).
Collins, J. et al., Proc. Natl. Acad. Sci., USA; 75, 4242-4246 (1978).
Grosveld, F. G. et al., Gene; 13; 227-237 (1981).
Lau, Y. F. et al., Proc. Natl. Acad. Sci., USA, 80: 5225-5229 (9-1983).
Steinmetz, M. et al., Nature, 300: 35-42 (11-1982).
Tonegawa, S. Nature, 302:575-581 (4-1983).
Davis, B. D. et al., *Microbiology*, 3rd ed., Harper & Row, Publisher, Philadelphia (1980), pp. 183-213.
Robertson, M., Nature, 306:733 (1983).
Rabbitts, T. H., et al., Nature 306:760 (1983).
Heisterkamp, N., et al., Nature, 306:239 (1983).
Bartram, C. R., et al., Nature, 306:277 (1983).
Kan, Y. W., et al., Proc Nat Acad Sci USA, 75:5631 (1983).
Orkin, S. H., et al., Nature, 296:627 (1982).
Orkin, S. H., et al., Prog Hematol, 3:49 (1983).
Davies, K. E., et al., Nucleic Acids Res, 11:2303 (1983).
Hayes, C. E., et al., Science, 223:559 (1984).
Zabel, B. H., et al., Proc Nat Acad Sci USA 80:6932 (1983).
Erlich, H. A., et al., Proc Nat Acad Sci USA 80:2300 (1983).
Maniatis, T., et al., *Molecular Cloning: A Laboratory Manual*, Cold Spring Harbor Laboratory, 280 (1982).
Blin, N., et al., Nucleic Acids Research, 3:2302 (1976).
Maniatis, ibid., 282.
Fangman, W. L., Nucl Acids Res, 5:653 (1978).
Schwartz, D. C., et al., Cold Sp.HSQB, 7:189 (1983).
Schwartz, D. C. et al., Cell (May, 1984), 37:67-75.
Dugaiczyk, A., et al., J Mol. Biol., 96:171 (1975).
Ryan, M. J., et al., J. Biol. Chem., 254:5817 (1979).
Maniatis, ibid., p. 300.
Langer, P. R., et al., Proc Nat Acad Sci USA 78:6633 (1981).
Hood, L., et al., Cell, 28:685 (1982).
Maniatis, ibid., 188, 212.
Kraus, J., et al., Proc Natl Acad Sci USA, 79:4015 (1982).
Barker, D., et al., Cell, 36:131 (1984).
Kaufman, J. F., et al., Cell, 36:1 (1984).
Gladstone, P., et al., Proc Nat Acad Sci USA 79:1235 (1982).
Maniatis, ibid., 284.
Ish-Horowicz, et al., Nucleic Acids Res, 9:2989 (1981).

Grosveld, F. G., et al., Nucleic Acids Res, 10:6715 (1982).
Maniatis, ibid., 115.
Maniatis, ibid., 109.
Maniatis, ibid., 304.
Maniatis, ibid., 392.
Harper, M. E., et al., Chromosoma (Berlin), 83:431 (1980).

*Primary Examiner*—Charles F. Warren
*Assistant Examiner*—Margaret Moskowitz
*Attorney, Agent, or Firm*—Ciotti, Murashige, Irell & Manella

[57] ABSTRACT

A junction-fragment DNA probe, a DNA probe cluster, and methods of preparing and using the probe and cluster to study gene localization and organization. The probe includes first and second gene segments which are derived from first and second, single-copy genomic-DNA gene regions, respectively, separated from one another, in the genomic DNA strand, by a selected distance of between about 20 and 2,000 kilobases. The two segments in the probe are connected at a junction region which may include a marker segment usable in isolating and/or selecting the probe. The probe cluster includes a set of such probes, each having a common first segment, and a second segment which is derived from one of a number of gene regions located at various distances from the first gene region in the genomic DNA strand from which the two segments are derived.

24 Claims, 7 Drawing Figures

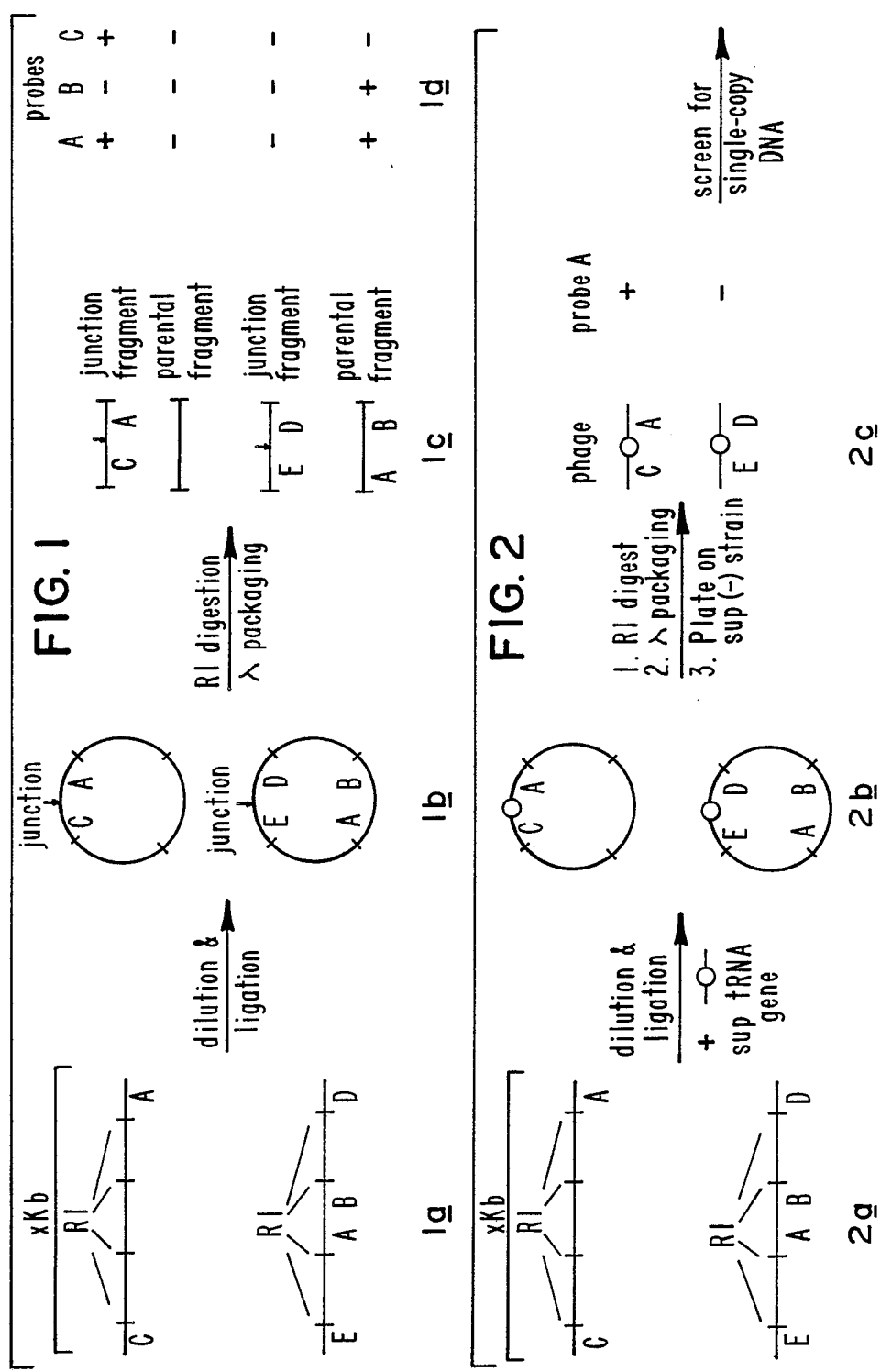

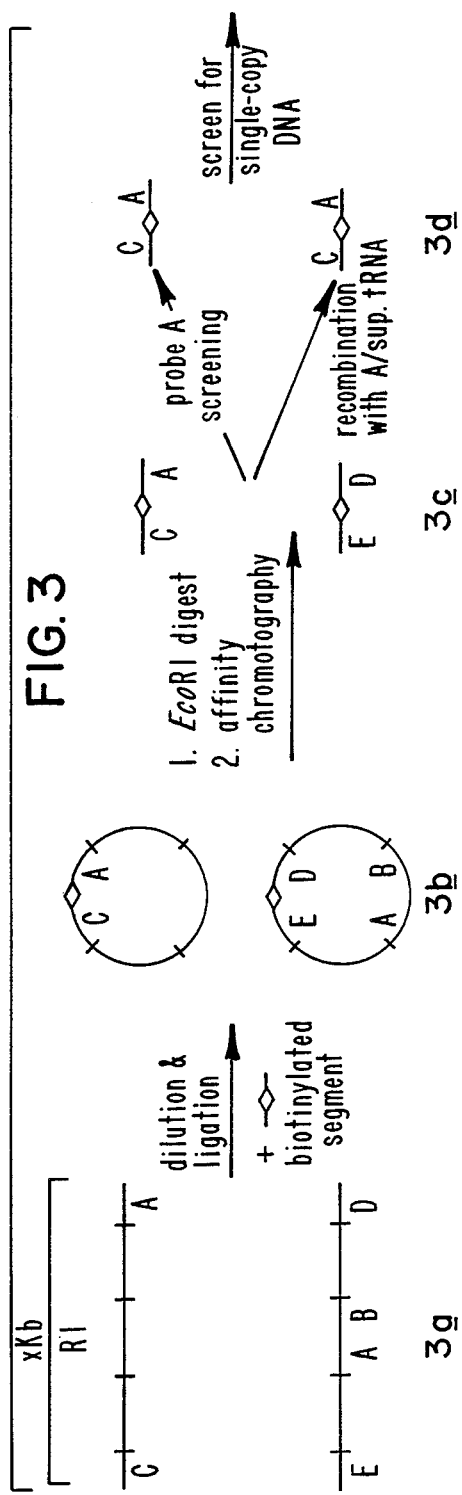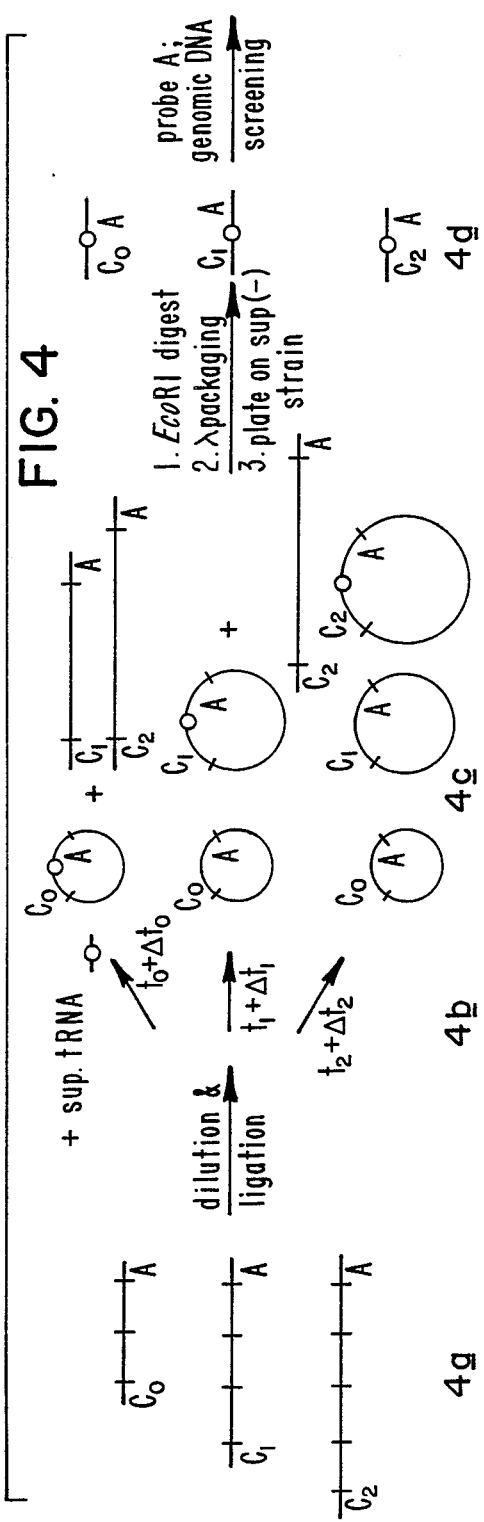

JUNCTION-FRAGMENT DNA PROBES AND PROBE CLUSTERS

The invention was supported in part by the National Institute of Health grant #NIH CA-30938 and the Government has certain rights to the invention.

BACKGROUND AND SUMMARY

The present invention relates to DNA probes and probe clusters useful for studying gene localization and organization.

The following references are referred to by corresponding number herein:
1. Robertson, M., Nature, 306:733 (1983).
2. Rabbitts, T. H., et al., Nature, 306:760 (1983).
3. Heisterband, N., et al., Nature, 306:239 (1983).
4. Bartram, C. R., et al., Nature, 306:277 (1983).
5. Kan, Y. W., et al., Proc. Nat. Acad. Sci. USA, 75:5631 (1983).
6. Humphries, S. E., et al., Med. Bull., 39:343 (1983).
7. Orkin, S. H., et al., Nature, 296:627 (1982)
8. Orkin, S. H., et al., Prog. Hematol., 13:49 (1983)
9. Davies, K. E., et al., Nucleic Acids Res., 11:2303 (1983)
10. Murray, J. M., et al., Nature, 300:69 (1982)
11. Gusella, J. F., et al., Nature, 306:234 (1983).
12. Steinmetz, M., et al., Nature, 300:35 (1982).
13. Hayes, C. E., et al., Science, 223:559 (1984).
14. Zabel, B. H., et al., Proc. Nat. Acad. Sci. USA, 80:6932 (1983).
15. Botstein, D., et al., Am. J. Human Genetics, 32:314 (1980).
16. Möller, G. (ed), Immuno. Rev., 70 (1983).
17. Erlich, H. A., et al., Proc. Nat. Acad. Sci. USA, 80:2300 (1983).
18. Maniatis, T., et al., *Molecular Cloning: A Laboratory Manual*, Cold Spring Harbor Laboratory, 280 (1982).
19. Blin, N., et al., Nucleic Acids Research, 3:2302 (1976).
20. Maniatis, ibid, 282.
21. Fangman, W. L., Nucl. Acids Res., 5:653 (1978)
22. Schwartz, D. C., et al., Cold Sp.HSQB, 7:189 (1983; Schwartz, D. C. and Cantor, C. R., Cell, (May, 1984)
23. Dugaiczyk, A., et al., J. Mol. Biol., 96:171 (1975)
24. Ryan, M. J., et al., J. Biol. Chem., 254:5817 (1979)
25. Maniatis, ibid, p. 300
26. Langer, P. R., et al., Proc. Nat. Acad. Sci. USA 78:6633 (1981)
27. Hood, L., et al., Cell, 28:685 (1982)
28. Maniatis, ibid, 187, 211
29. Kraus, J. and Rosenberg, L. E., Proc. Natl. Acad. Sci. USA, 79:4015 (1982)
30. Sood, A. K., et al., Proc. Natl. Acad. Sci. USA, 78:616 (1981)
31. Das, H. K., et al., Proc. Natl. Acad. Sci. USA, 80:1531 (1983)
32. Seed, B., Nucleic Acids Res., 11:2427 (1983)
33. Barker, D., et al., Cell, 36:131 (1984)
34. Steinmetz, M., et al., Science, 222:727 (1983)
35. Kaufman, J. F., et al., Cell, 36:1 (1984)
35 a. Gladstone, P., et al., Proc. Natl. acad. Sci. USA, 79:1235 (1982)
36. Maniatis, ibid, 284
37. Ish-Horowicz, et al., Nucleic Acids Res., 9:2989 (1981)
38. Grosveld, F. G., et al., Nucleic Acids Res., 10:6715 (1982)
39. Maniatis, ibid, 115
40. Maniatis, ibid, 382
41. Maniatis, ibid, 109
42. Maniatis, ibid, 304
43. Maniatis, ibid, 392
44. Godson, G. N. in *Methods of DNA and RNA Sequencing*, ed. Weissman, S. M. (Praeger, N.Y., N.Y.), pp 69–111 (1983).
45. Bayer, E. A. and Wilchek, M., Methods Biochem. Analysis, 26:1 (1980)
46. Harper, M. E. and Saunders, G. F., Chromosoma (Berlin), 83:431 (1980)

Gene localization on chromosomes and an understanding of gene organization within large gene groups have become important areas of study in human genetics. A major application of gene localization is in understanding and predicting certain disease states. For example, translocation of marker genes from one chromosomal region to another may play a role in the development of cancer cells. One of the known oncogenes in man and rodents, termedmyc, has been localized to a chromosome region which shows a consistent translocation from its normal chromosomal environment to one of three other chromosomes in certain forms of tumors such as Burkitt's lymphoma. Because the location of the genes for immunoglobulins was previously known, it could be determined that the chromosome segment always became translocated to a second chromosome region containing immunoglobulin genes. Further studies have shown that the myc oncogene is, in fact, located close to the boundary of the translocation point, suggesting that a basic mechanism and causation of this lymphoma is the movement of the oncogene from its normal chromosome environment to an immunoglobulin gene environment in a cell where the immunoglobulin genes are being actively expressed (reviewed in references 1 and 2). Similarly, translocation of the Ab1 oncogene may be a major determinant of chronic myelocytic leukemia (references 3 and 4).

Another important application of gene localization is in identifying and furthering an understanding of inheritable disorders. Restriction endonuclease analysis of genomic DNA has made it possible to identify DNA polymorphisms which are linked closely to normal or mutated genes associated with available probes (reviewed in references 5,6). The relationship between DNA polymorphisms and disease states was shown originally in studies on hemoglobinopathies, where certain polymorphisms are more frequent in patients with sickle cell disease, and where certain varieties of thalassemia are more commonly associated with specific combinations of restriction sites in intergenic DNA (references 7, 8). More recently, systematic studies have uncovered polymorphic DNA sites that are linked to and flank the locus of mutations which are responsible for Duchenne's muscular dystrophy (references 9, 10), and a fortuitously discovered probe associated with Huntington's disease has been used to identify polymorphic DNA which is closely linked to the gene responsible for Huntington's disease (reference 11). The probe makes it possible to diagnose people who carry the gene for Huntington's disease before the onset of the disease.

Heretofore, gene localization has been approached either by classical studies on gene linkage related to inheritance, or by microscopy and banding techniques for chromosomes. In the classical genetics approach, the frequency of co-inheritance of one phenotypic trait, whose gene location is unknown, with a phenotypic trait whose gene location is known provides a measure of the linkage (distance) between the two genes, and this distance provides a rough measure of the relative chromosome positions of the two phenotypic genes. The classical genetic approach is severely limited in man, where controlled breeding is not possible, and where family studies on the inheritability of phenotypic disorders must therefore be relied on. Family studies in man and even genetic studies in inbred strains of mammals are generally unable to resolve gene linkages located closer than about 5 to 10 million base pairs apart, and can give aberrant results that cannot be readily understood until the actual physical structure of the gene is known. As an example of the latter problem, the I-J gene of suppressor lymphocyte surface antigen was initially considered to be one of the genes of the major histocompatibility complex (MHC), and this error was only corrected when portions of the MHC were actually cloned and partially sequenced (references 12, 13).

Genomic DNA regions of unique sequence can, in principle, be localized on a chromosome by in situ hybridization using single-copy DNA probes. In situ hybridization of nucleic acid probes to spreads of polytene chromosomes in Drosophola have been remarkably successful. The polytene chromosomes, which may be amplified over a thousand fold, allow site-specific binding of up to a thousand or more probes at the same location, making probe detection by autoradiography or by fluorescence or enzyme-reporter microscopy quite straightforward. Unfortunately, in situ hybridization to-single-copy genes in human DNA is much more difficult to detect since only a single site is available for probe binding, and can only be identified autoradiographically with relatively long periods of exposure and by counting grains over many chromosome samples to obtain a sufficient distribution of grains to verify probe localization. With rare exceptions, and particularly where only non-polytene chromosomes are available, the in situ hybridization technique cannot distinguish between sequences located closer than about 5 to 10 million base pairs apart (reference 14), comparable to the resolution achievable with phenotypic markers in classical genetic studies. The in situ hybridization technique for locating genes on a chromosome are also subject to artifactual errors such as a tendency for grains to accumulate at the tip or at the center of a chromosome. Such an artifact may account for the still conflicting data from in situ hybridization studies as to whether the beta globin system is located near the tip of chromosomal 11, or closer to the centromere.

In studies on polymorphic DNA regions, discussed above, it has been possible heretofore to localize identified polymorphisms only in the relatively few chromosome regions for which marker probes have been available, such as in the MHC region. In principle, if a complete family of probes spaced evenly along the genome were available, it would be possible to screen individuals for inherited dominant or even recessive disorders, and by comparing many DNA polymorphic sites in the affected individuals and unaffected family members, to localize and derive markers (probes) closely linked with every disorder. This theory has been discussed previously (reference 15). Since there are approximately 3,000 centimorgans of recombination distance distributed along the human genome, 300 evenly spaced markers would provide a marker for every 10 centimorgans, and 600 markers, for every 5 centimorgans. The probability of recombination between such a polymorphic marker and the given disease marker would be less than 1 in 20 in each generation. This set of 300 or 600 markers would greatly facilitate localization and identification of the precise genetic effects in gene regions responsible for these inheritable effects.

In order to generate such DNA probes for identifying polymorphic fragments by prior art techniques, many random DNA segments must be analyzed to see which ones provide polymorphic markers. Each one of these markers ust be localized by the in situ hybridization technique described above, or by techniques involving hybridization and detection in a variety of somatic hybrid cell lines containing various human chromosomes or segments of chromosomes, or by hybridization to probs made from assorted chromosome libraries. The latte method is relatively inefficient due to the small amout of DNA that can be obtained in chromosomal sorting pocedures. Statistical studies indicate that 900 or ore probes would have to be examined in this way n order to obtain a 98% to 99% coverage of the human genome at the desired space intervals, a task thar would be exceedingly difficult at best.

Considering now investigations of gene relationships in m-lt-gene arrangements on chromosomes, the best-studied example is the human MHC, which appears to contin at least 40 to 50 class I-like genes, and at least 15 to 20 class II-like genes or pseudo-genes. It is nown that the MHC system is highly polymorphic from individual to individual, and that particular allels of class I or class II genes are associated with a predisposition towards a wide variety of diseases (references 16, 17). The association of polymophisms with particular disease states may be due to polymorphisms within the known genes of the MHC, or, alternatively, to polymorphisms in presently unidentiied class I or class II-type genes, or possibly unelated genes interspersed within the class I or class II system. Therefore, a complete characterization of all the genes contained within this cluster, and their linear relationship with one another, would make it possible to predict which genes are most likely to be closely associated with particular diseases.

A study of the relationship among genes in a gene cluster or family can lead to greater understanding of gene diversity, gene interaction, and even the identification of previously unrecognized gene products. It is known, for example, that at least two pituitary hormones are encoded by genes contained in a gene cluster. Mapping the genes in this cluster has the potential to uncover DNA sequences that are potential genes of other known pituitary hormones and also genes for hormone-like substances that have not been previously recognized, but which arose during evolution by tandem duplication or pre-existing genes for hormones.

As another example, it is known that there are many interferon-like genes in a cluster for one of the interferon types; similar clusters for interleukin-2 and other lymphokine genes, as well as for colony stimulating factor and nerve growth factors may be identified. Growth factors specific for several different cell types have been reported and it is possible that by mapping genes clustered about the growth factor genes, genes encoding other colony-stimulating factors or the like can be identified.

Similarly genes for additional coagulation factors, serum proteins, protease inhibitors, transcription or replication factors, cell membrane receptors, immunoglobulin variable or constant regions, and other cell type-specific surface antigens could well be identified by a practical method for surveying gene clusters.

The organization of genes within a gene family has been approachable, heretofore, generally at two levels of resolution. One is the resolution which can be obtained by classical studies of gene linkage during inheritance. As noted above, classical genetic techniques are unable to distinguish phenotypic markers located closer than about 5 to 10 million base pairs apart. The second level of resolution is that accessible by more recently developed recombinant DNA techniques. In a typical procedure, a genomic DNA insert which has been identified, for example, by hybridization with a selected gene probe, is characterized as to restriction sites and/or base sequence. Currently, the largest block of DNA that can be cloned intact is about 40 kilobases. The only method available in the prior art for extending the cloned sequence (beyond this 40 kilobase limit) is a technique known as hromosomal walking, in which the ends of the cloned insert are identified, radiolabeled and used as probes to isolate, from a library of cloned DNA inserts, one or more inserts having a region of overlap with the end region(s) of the original insert. On the average, the radiolabeled end probes will identify inserts whose region of overlap lies near the midpoint of the overlapping inserts. This means, for inserts of 40 kilobases, each additional insert isolated will extend the map region only about 20 kilobases.

The chromosomal walking technique is obviously quite tedious, in that each extension of the map requires screening a genomic DNA library, characterizing the restriction endonuclease sites and/or sequence of the probe-identified insert to locate the new insert in the map, and may require producing new end probes. Further, if one or more of the probes which are used in the procedure are non-unique sequences, these in turn will select for more than one site and cause apparent branching in the map. The maximum map distance that has been achieved to date by this method is about 200 kilobases, in a molecular map of an immune response region MHC, in which 18 overlapping inserts were identified (reference 12). This was a particularly favorable system since several probes scattered through the cluster were available.

It is thus apparent that (1) examining gene relationships in a gene region of up to 200 kilobases is generally difficult and uncertain by prior art methods; and (2) neither classical-genetic nor prior art cloning techniques are suited to resolving gene relationships in the range between about 200 kilobases and up to several thousand kilobases.

The present invention provides novel gene probes and gene probe clusters which can be readily designed, according to novel techniques of the invention, for studying questions of gene localization and organization which have been largely inaccessible by prior art genetic analysis methods, discussed above.

A particular object of the invention is to provide a cluster of gene probes for use in localizing a single copy gene region in mammalian and, in particularly, human chromosomes.

Another object of the invention is to provide a method for generating a family of single-copy DNA fragments which are derived from genomic DNA regions located substantially uniformly along the chromosomes of the genome, at an average spacing from one another such that at least one fragment will show some linkage during inheritance to substantially any disease related gene.

Another specific object of the invention is to provide probes, and methods of preparing same, for studying gene relationships and organization particularly within a region between about 50 and 2,000 kilobases.

Yet another object is to provide a system for rapidly surveying an extensive gene cluster to identify other expressed genes.

According to one aspect of the invention, there is formed a novel probe is connected adjacent the downstream end of the downstream end of the second segment, either by direct ligation, or through a marker segment which allows selection and/or isolation of the probe. In one embodiment of the invention, the marker segment includes a suppressor tRNA which allows for selection of a phage vector containing the probe in a suppressor (−) host. In another embodiment, the marker segment includes a cos site which allows for selection of a cosmid vector containing the probe as an insert. In still another embodiment, the marker segment includes a ligand by which the probe can be isolated by specific binding to an anti-ligand.

The gene probe is constructed, according to a method of the invention, by providing randomly sized pieces of genomic DNA, which may be size fractionated to yield a selected size distribution within a range of sizes which may vary from about 20 to 2,000 kilobases. The DNA pieces are ligated under conditions which produce predominantly circularized monomers, and the monomers are digested with one or more selected restriction endonucleases to release fragments containing opposed end segment of the pieces joined at a junction region. The desired gene-probe fragments are selected by the presence of segments which hybridize to at least one end-segment probe and/or by the presence of a marker segment in the fragment.

A gene probe cluster of the invention includes a group of such gene probes, each having a first segment which is complementary to a common gene region of genomic DNA, and a second segment which is complementary to one of a series of second gene regions located downstream of, and at increasingly spaced intervals from the first gene region of the genomic DNA.

The gene probe cluster may be produced by applying the gene probe construction method described above to a series of size-fractionated groups of DNA, or by incorporating a marker segment selectively into different size distributions of unfractionated DNA pieces, as the pieces are being ligated to form circularized monomers.

Also forming part of the invention are novel methods which use the gene probe or probe cluster of the invention to:

1. determine the distance between, and/or orientation of two known genomic gene regions which are separated by a gene spacing of between about 20 and 2,000 kilobases;

2. determine the identity of a gene region which is separated from a known gene region by a gene spacing between about 20 and 2,000 kilobases;

3. generate a series of single-copy probes derived from gene regions which are substantially evenly spaced along genomic DNA by a distance of between about 100 and 2,000 kilobases;

4. localize the chromosomal position of any single-copy gene for which a gene probe exists; and 5. map the identity and positions of genes in a gene family which may cover several thousand kilobases of genome.

These and other objects and features of the invention will become more fully apparent when the following detailed description of the invention is read in conjunction with the accompanying drawings.

BRIEF DESCRIPTION OF THE DRAWINGS

FIG. 1 illustrates steps for producing and selecting desired junction-fragment gene probes according to one embodiment of the invention;

FIG. 2 illustrates steps for producing and selecting desired junction-fragment gene probes according to a second embodiment of the invention;

FIG. 3 illustrates steps for producing selected junction-fragment gene probes according to yet another embodiment of the invention;

FIG. 4 illustrates steps for producing a cluster of gene probes according to an embodiment of the invention.

DETAILED DESCRIPTION OF THE INVENTION

Figure 5:
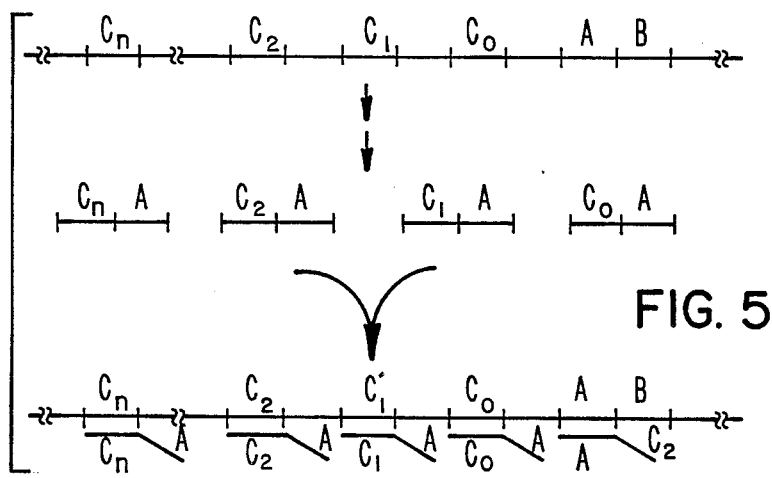
FIG. 5 illustrates a method for localizing a chromosomal gene region with a cluster of gene probes constructed according to the present invention.

Sections I-V below detail steps in the construction of a gene probe or gene probe cluster in accordance with the invention. The steps include first, fragmenting strands of genomic DNA to produce pieces which preferably have random sizes predominantly above a selected minimum length, such as 50 kilobases, as described in Section I below. These random-size DNA pieces may be size-fractionated by one of a variety of methods described in Section II, to produce groups of DNA pieces which are distributed substantially in defined size ranges. The DNA pieces are ligated under conditions which lead predominantly to monomeric circles of DNA formed by a single-piece, end-to-end ligation. The ligation reaction, including a reaction in which a marker segment is incorporated in the junction region of the monomeric circles, are described in Section III. Also described in this section is a reaction method for incorporating a marker segment selectively into different size groups of circularized monomers formed from unfractionated DNA pieces.

Following monomer formation, the circularized DNA pieces are digested with one or more selected restriction endonucleases, according to procedures described in Section IV, to produce digest fragments, a portion of which contain the junction regions of the circularized monomers. The junction-containing fragments (junction fragments) of interest are those having at least one gene segment derived from a known single-copy gene region. These fragments may be identified by one or a combination of a number of selection procedures described generally in Section V below.

Section VI considers methods for localizing a chromosome region of interest with the gene probe cluster of the present invention. Section VII describes a method for producing a series of single-copy gene probes derived from single-copy gene regions which are located at substantially equal intervals along the length of the genome, useful for identifying polymorphisms linked to disease-related genes. Section VIII illustrates the application of the gene probe cluster of the invention to studying gene organization and relationships in a gene family.

I. Producing DNA Pieces

The source of genomic DNA from which the DNA pieces are derived will typically be a particular cell type, cell line or tissue containing the DNA which is to be studied. For example, investigations of the major histocompatibility complex (MHC) in man have been carried out with DNA derived from peripheral blood lymphocytes or macrophages obtained from normal or individuals having known disease-related genetic defects (reference 12). Clonal sublines derived from lymphocytes, which therefore have a relatively uniform genetic composition, may be preferred. The cell line may be selected for specific chromosomal aberrations, such as a chromosomal deletion in the chromosomal regions of particular interest. To illustrate, a stable human B-lymphoblastoid cell line having a deletion of the short arm of one copy of chromosome 6 has been prepared (reference 17). This deletion is known to extend to the MHC genes for DR, DC, SB and HLA and B. Accordingly, studies on the localization and/or organization of these genes is unambiguous as to alleles, since only one copy of the genes is present in the chromosomes from the cell line.

DNA from the cell source is isolated by standard procedures, which typically include successive phenol and phenol/chloroform extractions with ethanol precipitation, as described generally in references 18, 19. In Example I below, peripheral blood lymphocytes derived from normal individuals were employed as a source of genomic DNA, and the DNA was isolated by successive phenol and phenol/chloroform extractions.

A variety of methods are available for fragmenting the isolated DNA into DNA pieces having the desired size distribution. Mixtures of DNA pieces whose sizes are predominantly 50 kilobases and greater may be produced, according to standard procedures, by partial restriction endonuclease digestion of the isolated DNA, Sau3A or BamHI. Procedures for establishing conditions of partial digestion of high-molecular weight DNA have been described (e.g., reference 20), and generally include monitoring, by gel electrophoresis, the extent of DNA digestion as a function of reaction time or restriction endonuclease concentration.

Although DNA pieces may also be formed by known mechanical shearing methods, this approach is generally disadvantageous in that the sheared fragments must be first reacted with polylinkers to attach sticky ends to the pieces before the fragmented pieces can be circularized, in accordance with the invention.

II. Fractionating DNA Pieces

In most cases, it is advisable to fractionate the restriction endonuclease digest pieces to remove small fragments, which tend to concatemerize with other DNA pieces in the circularization reaction described in Section III below. Ultracentrifugation of the DNA pieces through a sucrose gradient is a preferred method of removing small molecular weight pieces, since this technique is relatively simple, and can handle large volumes with substantially complete recovery of the larger DNA pieces. In a typical procedure, described in Example I, the DNA sample is heated briefly to inactivate nucleases, loaded on a sucrose density gradient and ultracentrifuged for a several-hour period sufficient to effect the required size separation. In a typical separation, the greater size separation occurs in the approximately 1 to 40 kilobase region, with fragments larger than this being concentrated at the bottom of the gradient. Successive gradient fractions are collected, for example by dripping the gradients slowly from a puncture hole in the bottom of the tube, and the various samples are analyzed for size distribution by gel electrophoresis. The samples containing the smaller pieces are discarded.

Fractionation of large relatively large DNA pieces (in the approximately 50–1,000 kilobase region) can be achieved by density gradient fractionation, or preferably, by gel electrophoretic techniques. Electrophoresis using 0.2% agar to achieve resolution of DNA pieces in the 50 to 500 kilobase size range has been described (reference 21). More recently, a two-dimensional pulse field gradient (PFG) electrophoretic method which allows resolution of DNA molecules of up to 2,000 or more kilobases long has been reported (reference 22). DNA digestion and gel electrophoresis may be performed in a simple 2-step procedure in which the DNA digestion is carried out in agarose matrix, and the digest particles are electrophoresed directly from the agarose matrix into an agarose slab (reference 22). Size-fractionated DNA pieces are recovered readily from a gel matrix by conventional techniques involving electroelution and DNA extraction.

III. Circularizing DNA Pieces

According to an important step of the invention, the random-size or size-fractionated DNA pieces are ligated under conditions which produce predominantly circular monomers containing end-to-end junctions. The general theory of DNA segment ligation as it relates to monomer and concatemer formation has been discussed (reference 23). The theory, which is based on the probability of end-ligation occurrences, predicts the concentration of DNA pieces, j, at which the probability of DNA circle formation is equal to the probability of formation of linear concatemers. For large molecular weight DNA molecules, $$j = \frac{63.5}{(kb)^{\frac{1}{2}}} \text{ micrograms/ml,}$$

where kb is the length of the DNA in kilobases. The equation predicts, for example, that for 50 kilobase DNA pieces, j is approximately 9 micrograms/ml.

The concentration of DNA pieces in the ligation reaction is selected to produce a high percentage (e.g., 95%) of circularized monomers in the completed reaction. To determine this concentration, the mixture of DNA pieces to be ligated is diluted to a number of increasingly dilute mixtures. The highest concentration is preferably about that predicted by the above equation to produce approximately equal number of circularized monomers and linear concatemers, and the lowest concentrations are typically between about 10 to 100 times more dilute. The various-dilution DNA mixtures are incubated with a suitable ligase enzyme, such as T4 DNA ligase, at a suitable activity concentration, such as between about 1 and 2 units per microliter, under conditions which produce substantially complete ligation. Generally, the reaction time required to achieve complete ligation will increase with longer DNA pieces.

In Example IV below, the ligation of a 45 kilobase cosmid B1 insert from Example II to form monomeric circles is examined. The DNA pieces, which were prepared at concentrations between 0.6 and 30 micrograms per ml, were mixed with 1.6 units per microliter of T4 DNA ligase, and the reaction carried out at 12° C. for 12 hours. The percent circle formation achieved at each of the different concentrations of DNA pieces was determined by treating the ligation mixtures with EcoRI to produce digest fragments—a portion of which span the end-to-end ligation junctions—and analyzing the fragments produced for the presence of end segment regions, as evidenced by the ability of the fragments to hybridize end-segment probes. The results, shown in TABLE I of Example IV, show that substantially complete (about 96%) monomer formation is achieved at 0.6 micrograms DNA pieces per ml.

The requisite concentration, $j_x$, of larger DNA pieces of x kilobase size, can be calculated from the above equation as follows:

$$j_x = 0.6 \frac{(50)^{\frac{1}{2}}}{(x)^{\frac{1}{2}}} \text{ micrograms/ml}$$

Thus, for example, the concentration of DNA pieces having a molecular weight of about 180 kilobases would be about 0.3 micrograms per ml. It may also be necessary to extend the reaction time beyond 12 hours to achieve substantially complete ligation for the larger size segments.

The specific reaction described above is one in which the DNA pieces are ligated directly end-to-end to produce circular monomers. This method is illustrated in frames 1a and 1b of FIG. 1. According to another important aspect of the method of the invention, the reaction may be carried out under conditions in which a marker segment is incorporated into the junction. The marker segment may be one which permits biological selection of monomer fragments containing the marker, referred to generally as a selectable marker, or one which permits physical separation of marker-containing fragments, for example by affinity chromotography, referred to as a ligand marker. It is important that the marker gene be sufficiently small (less than about 300 base pairs) so that it cannot self-circularize. One exemplary selectable marker includes a suppressor tRNA gene which allows amber-mutated phage lambda containing the suppressor gene to grow in suppressor-free hosts (reference 24). The suppressor tRNA gene may need to be modified by attaching linker segments capable of forming sticky-end attachment to the DNA pieces during the circularization reaction. Example V below describes the preparation of a suppressor tRNA marker gene having BamHI sticky-ends. To incorporate the suppressor gene into circularized monomers, the tRNA gene is included in the ligation reaction at a several-fold molar concentration excess with respect to the DNA concentration, and the mixture of DNA pieces and marker gene segments are ligated under the conditions described above for direct-end ligation. This method is illustrated in frames 1a and 1b of FIG. 2 and described in Example VI. Methods for selecting junction-fragments containing the suppressor tRNA in a suppressor-minus host are described in Section IV below.

Cos sites, which are carried in plasmids known as cosmids, are another type of selectable marker which may be incorporated into the junction region of monomers. The essential characteristics of cosmids, and their use in cloning eukaryotic DNA fragments up to 45 kilobases, are well known. The cosmid vector selected is preferably one which has a unique restriction endonuclease site which will allow sticky-end ligation with the DNA digest pieces. The cosmid vector is linearized at this endonuclease site, and may be further treated with alkaline phosphatase (reference 25) to prevent self ligation in the monomerization reaction. The linearized, phosphatase-treated cosmid vector is added to the DNA digest pieces, preferably at a 10-25 molar excess, and the reaction components are ligated, in the presence of a suitable ligase under conditions substantially like those described above. The reaction produces circularized monomers containing one or more junction-site cosmid vector segments. These are then subjected to partial digestion and recircularization, followed by selection of junction fragments in a conventional phage lambda cloning system, as will be described in Section IV. The cosmid cloning and selecting techniques described in Example II are generally applicable.

Self-ligation of the cosmid vector in the circularization reaction can be minimized, as indicated above, by treating the vectors with alkaline phosphatase. A more elegant approach which avoids the problem of self-ligation of the vectors employs an approximately 18 base cos site marker segment. The cos site is preferably produced as a synthetic polynucleotide which includes sticky ends capable of ligation with the sticky-end DNA digest pieces. The ligation reaction mixture includes the DNA pieces, at the suitably low concentrations indicated above, a 10-100 fold molar excess of the sticky-end cos site, and a suitable DNA ligase. The components are reacted under conditions similar to those described above, producing circularized monomers having one or more of cos sites at their junction regions. For selection purposes, the fragments are spliced into a plasmid containing an origin of replication site requisite for cosmid replication in a bacterial host system. The cos-site fragments are selected on this host as described in Section IV.

Ligand-type marker segments include a ligand portion or moiety capable of binding specifically and with high affinity to an anti-ligand to form a ligand/anti-ligand complex. The ligand portion may be a length of single-stranded nucleic acid capable of hybridizing with a complementary "anti-ligand" strand, or may be an antigen ligand having a specific anti-ligand binding pair. Examples of such ligand/anti-ligand pairs include antigen/antibody carbohydrate/lectin, biotin/avidin and DNA sequence/sequence-specific binding protein pairs. The latter type of binding pair is illustrated by the lac operator/lac repressor protein. Where the ligand moiety is an antigen ligand, the marker segment preferably includes a length of typically double-stranded DNA having one or more antigen molecules coupled covalently to the nucleic acid bases. One preferred ligand includes biotin which binds specifically and with high affinity to both avidin and to anti-biotin antibody. A method for attaching biotin covalently to the C-5 position of uridine, to form a biotinylated dUTP, is described in reference 26. An application of the method to form a biotin-containing marker segment is described in Example VII where the biotin molecules are incorporated, as biotinylated dUTP, into filamentous bacteriophage M13 fragments. The significance of this approach is that only one strand of DNA is biotinylated, so that the other strand can serve as parent for viable progeny. The biotinylated fragments are incorporated into circularized DNA pieces substantially as has been described for selectable marker segments, as illustrated in frames 1a and 1b of FIG. 3, and as described in Example VII.

A cluster of junction-fragment gene probes, each derived from a different size-distribution of DNA pieces, can be prepared by ligating each of several size-fractionated DNA mixtures to completion under the ligation conditions just described. This method of generating a probe cluster is illustrated in Example IX. A second general reaction method for generating a cluster of junction-fragment gene probes derived from different-size DNA fragments, which will now be described, takes advantage of the statistically more rapid circularization of relatively small DNA pieces which occurs during the ligation reaction.

From kinetic considerations, the rate of circularization of a linear molecule will be proportional to the j concentration defined above. For two DNA fragments 1 and 2 of length $Kb_1$, and $Kb_2$, present in equivalent molar concentrations in solution, their relative initial rates of circularization, $r_1$, and $r_2$ respectively will be $$\frac{r_1}{r_2} \; \frac{j_1}{j_2} \; \frac{Kb_2^{\frac{3}{2}}}{Kb_1}$$

In other words, the initial rate of circularization of a 50 Kb molecule is twice as rapid as that of a 200 Kb molecule.

The procedure is illustrated very schematically in FIG. 4. Initially, unfractionated DNA digest pieces are divided to form several preferably equal-volume reaction mixtures, each containing a range of sizes of DNA pieces, such as those indicated in frame 1a of FIG. 4. The reaction in each mixture is initiated at time $t_0$ by the addition of suitable DNA ligase, and to one of the mixtures is also added a 10-100 fold molar excess of either a selectable or ligand marker segment. After a reaction period $\Delta t_0$ sufficient to allow a relatively small portion of the DNA pieces to ligate, the ligation reaction in the mixture containing the selectable marker is terminated, yielding a relatively small portion of circularized fragments, a portion of which have incorporated the marker segment into their junction region, and a greater portion of non-circularized pieces. Because of the statistically greater number of smaller pieces which circularize during the initial ligation period $\Delta t_0$, circularized fragments containing the marker segment are skewed toward monomers derived from relatively small DNA pieces. Characteristically, $\Delta t_0$ will be between about 5 and 60 minutes, depending on reaction concentration conditions and the degree of size resolution which is desired.

At a second time $t_1$ during the ligation reaction period, the same marker segment is added to a second mixture, and the ligation reaction is allowed to proceed for a period $\Delta t_1$ to incorporate the segment into a portion of the DNA pieces which circularize, during this second interval. As suggested in frame 1b of FIG. 4, the DNA pieces which circularize during the $\Delta t_1$ interval statistically are larger than those which have circularized during the $\Delta t_0$ interval. The mixture, therefore, contains relatively small circularized monomers which do not contain the marker segment and larger circularized monomers which do, plus relatively large uncircularized pieces. The $\Delta t_1$ interval will typically be somewhat longer than the $\Delta t_0$ interval, in order to produce marker segment incorporation into approximately the same number of circularizing DNA pieces.

Similarly at a later time $t_2$, the marker segment is added to a third group which is then allowed to react with the segment over $\Delta t_2$ interval, to incorporate the marker into still larger DNA pieces, on a statistical basis, as indicated at the lower portion of frame 1b of FIG. 4. The marker segment is added to successive groups, at increasing times and for increasingly longer time intervals, to incorporate the marker segment similarly into increasingly larger DNA pieces. Example X below illustrates this procedure as it is applied to incorporate suppressor tRNA into successively larger-size DNA monomeric circles.

IV. Producing Junction Fragments

The circularized monomers formed in accordance with Section III are treated with a selected restriction endonuclease or endonucleases to release fragments which contain the end-to-end junction of each monomer and the adjacent end segments derived from the opposite end regions of the DNA pieces forming the monomer. The junction fragments are formed by digesting the monomers to completion with a single restriction endonuclease, selected according to clone structure, which acts to cleave the monomer at a distance of several thousand base pairs from either, side of the end-to-end junction site(s), or the monomers are partially digested to generate fragments of a size suitable for cloning in lambda vectors, such as lambda XCh4A, or in cosmids. The endonuclease, of course, must not have a recognition site in the junction region of the monomers. Example IV below details a method for releasing junction fragments from circularized monomers by EcoRI digestion.

Describing the generation of junction fragments with reference to FIG. 1, frame 1a of this figure shows two different DNA pieces, one having an end-adjacent segment indicated at A and a second piece having internal A and B segments. Each of the two fragments have four EcoRI sites as indicated. Dilution and ligation of the two fragments, performed in accordance with Section III, produces the corresponding circular monomers shown in frame 1b of FIG. 1. The upper monomer includes end-adjacent A and C segments joined together at an end-to-end junction region and bounded by two EcoRI sites as shown. The other monomer contains end-adjacent D and E segments joined together at an end-to-end junction region which is also bounded by EcoRI sites, as indicated, and which is positioned opposite the A/B region as shown. Digestion of the upper monomer produces an A/C junction fragment and three parental fragments which contain neither A nor C segments. Digestion of the lower monomer produces a single junction fragment which contains neither A nor B segments, a parental fragment which contains both A and B segments, and two parental fragments which contain neither segment. Methods for selecting the desired A/C junction fragment from the other endonuclease digest fragments will be detailed in Section IV below. It suffices at this point to note that the desired A/C junction fragment includes a first segment derived from the A gene region located at one end of a DNA piece or fragment, a second segment derived from the other end of this piece, and a direct end-to-end junction or connection between the two segments. If the orientation of gene region C is arbitrarily designated as downstream of gene A, it can be appreciated that the junction joins the downstream end of segment C to the upstream end of segment A. Moreover, it is clear that the junction fragment, which does not include the 20–2,000 kilobase region between the A and C gene regions of the DNA piece from which the junction fragment was derived, is substantially shorter than this DNA piece.

More generally, the junction fragment of the invention includes a first segment which is derived from a first gene region of a fragment of DNA, and a second segment which is derived from to a second gene region positioned downstream of, and spaced from, the first gene region of the DNA fragment, by between about 20–2,000 kilobases, where the downstream end of the second segment is connected adjacent the upstream end of the first segment.

Where, such as in the examples illustrated in FIGS. 2 and 3, the junction fragment contains a marker segment the junction-fragments which are produced by restriction endonuclease digestion will contain end segments joined by the marker segment, which may be a selectable marker segment such as illustrated in FIG. 2, or a ligand marker segment as illustrated in FIG. 3. The only additional consideration in producing junction fragments containing marker segments is that the restriction endonuclease used to cut the circularized monomers does not produce cleavage in the marker segment region of the monomers. Preferably, and particularly where a selected restriction endonuclease produces the desired lengths of end segments in the junction fragment, the marker segments are constructed to contain no recognition site(s) for the selected restriction endonuclease. Thus, in Examples V and VI, where marker segment-containing junction fragments are produced by EcoRI digestion of circularized monomers, the suppressor tRNA marker segment was constructed, according to Example V, to eliminate end-segment EcoRI sites. Similarly, the biotinylated marker segments employed in Example VII were selected from double-stranded bacteriophage pieces which had been previously digested with EcoRI and made blunt-ended by reaction with *E. coli* polymerase, to eliminate EcoRI sites.

IV. Selecting Junction Fragments

One important feature of the selection step of the invention is that the junction fragments which are selected include at least one end segment which is derived from an isolated single-copy region of the genomic DNA. As will be seen, selecting junction fragments containing this single-copy region generally requires a probe derived from the region. The probe may be one which is available from studies on gene localization or organization. For example, studies on the MHC have led to the identification of a number of cloned inserts corresponding to single-copy regions of the MHC, providing a number of probes for selecting junction fragments derived from the MHC (reference 27). Similarly, a number of restriction fragment length polymorphisms (RFLP) which have been identified and shown to have a linkage relationship in human pedigrees to inheritable diseases provide another group of useful probes.

Copy DNA (cDNA) probes corresponding to single-copy genes which are functionally active in protein synthesis are also useful probes and can be obtained by copying messenger RNA (mRNA) isolated from cells active in protein synthesis. The mRNA is typically extracted as a poly A RNA fraction, and may be size fractionated, for example by gel electrophoresis, to yield RNA corresponding to a particular-size gene product. Techniques for isolating, size-fractionating and copying messenger RNA to produce clonable cDNA's are described generally in reference 28. Immune precipitation of polysomes carrying nascent polypeptide permits isolation of an mRNA fraction enriched in a selected mRNA species, as discussed, for example, in reference 29. A more recent method involving nucleic acid primer extension exploits very limited amino acid sequence data from a selected polypeptide to produce a synthetic polynucleotide which can combine directly to, and be extended on, the corresponding gene region of single-stranded genomic DNA. The extended double-stranded regions can be selectively cleaved and directly used as a probe for genomic clones without going through a cDNA intermediate (references 30, 31).

DNA probes derived from random, single-copy regions of genomic DNA can be produced by conventional cloning techniques in which random digest fragments of genomic DNA are cloned and screened for single-copy inserts. A refinement of this general procedure, which is described in Example III, provides DNA probes corresponding to end segments of a cloned DNA insert in the 35–45 Kb size range.

For each of the probe types described above, the probe may be cloned in a suitable cloning vehicle, and radiolabeled conventionally by nick-translation for use in probe-hybridization studies, such as in Southern-blot analysis.

The use of single-copy probes for selecting desired junction fragments will be considered first with reference to junction fragments that have been formed by direct end-to-end ligation. With reference to FIG. 1, region A represents a DNA region whose localization, orientation and/or relationship with one or more adjacent genes is to be investigated. As a first case, it is assumed that probes derived from the spaced gene regions A and C (upper fragment in frame 1a) are available. This case would apply, for example, where the junction fragments of the invention are used to study the spacing and/or orientation between known regions A and C. After digesting the circularized monomers to form the various junction and parental fragments shown in frame 1c of FIG. 1 (Example IV), these fragments are cloned and screened for the ability to hybridize probe A and probe C. As seen in frame 1d of FIG. 1, only the desired A/C junction fragment will hybridize both probes, whereas parental fragments containing either A or C gene regions will hybridize with one or the other of the probes only. One preferred method for cloning and screening the fragments, described in Example IV, includes ligating the fragments in a suitable restriction endonuclease site in bacteriophage lambda, infecting an E. coli host with the packaged lambda, fixing the plaques on nitrocellulose filters, and hybridizing the DNA on the filters with nick-translated probe A or probe C.

In a second general case, a pair of probes corresponding to the A region and an immediately adjacent B region, as indicated in the lower insert of frame 1a of FIG. 1, are available. With reference to frame 1d of this figure, it can be appreciated that selection of the cloned junction fragments by probes A and B will identify A-containing junction fragments as those which hybridize A but not B, and will identify, A-containing parental fragments as those which hybridize both A and B. It is also seen from FIG. 1 that a junction fragment containing segment A but not segment B will have formed from a DNA piece in which the end segment opposite end segment A will always be located downstream of A, i.e. in the direction opposite the A to B direction. Accordingly, in any selected A/$C_i$ junction fragment, the orientations of A with respect to $C_i$ will be known.

A second general procedure for selecting direct end-to-end junction fragments containing at least one isolated end segment involves the recombination and selection technique reported in reference 32. In this procedure, a recombination sequence corresponding to a selected gene region, such as region A of the DNA pieces in FIG. 1, is inserted into a small plasmid vector which is then introduced into recombination-proficient host bacterial cells. The plasmid also contains, adjacent the heterologous probe sequence, a selectable marker gene, such as suppressor tRNA gene, which can be used to provide selection for vectors which acquire the marker gene by recombination. Suitable plasmid vectors, recombination-proficient bacterial cells and methods for introducing the probe sequence and selectable marker into the plasmid vector are described in reference 32 and reference 18, pp 353–361.

To select junction fragments which contain a selected gene region, such as the A gene region in FIG. 1, the recombination-proficient bacterial cells are infected with bacteriophage libraries of the fragments, leading to homologous-reciprocal recombination between the probe region of the plasmid (i.e., the A region) and the homologous region of junction fragment carried in the infecting bacteriophage. This recombination yields phage bearing an integrated copy of the probe plasmid and the suppressor tRNA selectable marker gene from the plasmid. The phage are then used to infect a suitable suppressor-free bacterial host. A plaque will contain phage lambda having the desired A region-containing segment. With reference to frame C of FIG. 1, these fragments include both A/C junction fragments and A/B parental fragments. The junction fragments are selected from the parental fragments by screening with either probe A or probe B in accordance with the rationale and methods discussed above. This method is considerably faster than the 2-probe screening method described above, first, because the screening step involves only one probe, and secondly, because the number of plaques which must be screened with the probe is relatively small.

FIG. 2 illustrates a procedure for selecting junction fragments which have incorporated one or more selectable marker genes, in this case the suppressor tRNA gene, into the junction region. The procedure is like the homologous recombination selection procedure described above, except that here the selectable marker is inserted directly into the junction fragment during monomer formation, rather than through a recombination event involving cloned junction fragments. With reference to frame 1b in FIG. 2, circularized monomers, a portion of which contain suppressor tRNA at their junction regions, are treated with a selected restriction endonuclease, such as EcoRI, to produce junction and parental fragments whose end segment compositions are similar to those shown illustrated in frame 1c of FIG. 1. These fragments are spliced conventionally into bacteriophage lambda, which are then packaged by conventional in vitro methods and used to infect a suitable suppressor (−) bacterial host strain. The host strain is plated under conditions which allow for plaque development in cells infected with suppressor (+) lambda phage. As shown in frame 1c of FIG. 2, this procedure selects for phage carrying only junction fragments which have incorporated suppressor-tRNA at the junction site. The desired A/C junction fragments are selected by screening the phage-infected plaques with a selection probe, such as probe A. The selected A-region junction fragments are preferably screened further by a standard blotting technique, using total nick-translated genomic DNA, to identify those junction fragments which are single copy in both end segments. Example VI below details methods for incorporating a suppressor tRNA into monomeric circles, and for selecting suppressor tRNA-containing junction fragments whose end segments are derived from single-copy regions.

This and the following methods allow production of extensive junction fragment libraries that can be used repeatedly for generation of probe clusters.

A third general selection procedure, described with reference to FIG. 3, is applicable to junction fragments containing a ligand marker segment at the junction region. Circularized monomers, which are shown in frame 1b of FIG. 3, are digested with a selected restriction endonuclease, such as EcoRI, and the ligand-containing junction fragments are separated from non-ligand containing fragments by their ability to bind specifically and with high affinity to an anti-ligand. Preferably, the anti-ligand is carried on a solid support, allowing fragment separation by conventional affinity chromotography. In the method described in Example VII, biotin-labeled junction fragments are separated from other EcoRI digest fragments by affinity chromotography on a sepharose solid support prepared to contain surface-coupled anti-biotin antibody. After fragment-binding and column-washing steps, the bound fragments are released by elution with a high salt/urea solution.

The selected ligand-labeled junction fragments are spliced into a suitable cloning vector, such as bacteriophage lambda, to clone the fragment inserts. Plaques of a suitable bacterial host infected with the phage lambda may be screened for junction fragments containing a desired gene region, e.g., the A region of FIG. 3, and for single-copy end segments, by successive screenings with probe A and nick-translated genomic DNA, substantially as described with respect to FIG. 2. Alternatively, junction fragments containing the probe A gene segment may be selected by the plasmid-recombination method described above (reference 32), allowing selection of region-specific junction fragments according to the appearance of plaques in an infected, suppressor (−) host. The latter procedure, involving ligand-specific selection in conjunction with gene region-specific recombination selection, allows the desired junction fragments containing the selected gene region to be isolated without probe screening, and is therefore a relatively efficient method for identifying desired junction fragments. The selected junction fragments may be further screened by total genomic, nick-translated DNA for fragments in which both end segments are single-copy gene segments.

The selection methods described above are generally applicable both to selection of individual junction-fragment gene probes, and to clusters of gene probes. In the cluster of gene probes formed in accordance with the invention, each probe includes a first segment which is complementary to a first region of genomic DNA, such as gene region A shown in the figures, and a second segment which is complementary to one of a series of second gene regions located at increasingly spaced intervals from the first gene region, such as increasingly spaced gene regions $C_0$, $C_1$ and $C_2$ illustrated in frame 1a of FIG. 4. Preferably both segments in each probe are derived from single-copy gene regions.

With reference to FIG. 4, which illustrates one method for selecting a cluster of junction fragment probes, the three groups shown in frame 1c of the figure are each digested to completion with EcoRI to produce junction and parental fragments. Bacteriophage lambda containing the fragments is packaged and plated on a suppressor (−) bacterial host strain. Only those junction fragments containing a suppressor tRNA marker segment at the junction region will produce plaques in the host cells. Each group of plaques in screened individually with probe A to identify junction fragments containing the selected gene region A, as shown in frame 1c of this figure. The selected junction fragment probes may be further screened by nick-translated total genomic DNA to identify those junction fragments whose other end segments are also single-copy gene regions. As indicated, the selected cluster of probes include $A/C_0$, $A/C_1$ and $A/C_2$ probes, where statistically, $C_0$, $C_1$, $C_2$ are increasingly spaced from region A in the genomic DNA. Examples IX and X detail methods for producing a cluster of probes derived from size-fractionated and unfractionated DNA pieces, respectively.

VI. Localizing a Chromosomal Region of a DNA Probe

One important application of the gene probe cluster of the present invention is in localizing the chromosomal region of a known, single-copy probe in in situ hybridization. The known probe is one derived from a single-copy gene region of interest, which may include a functionally active gene, a region of identified DNA polymorphisms, or a random, single-copy gene region. Several sources and methods of producing such probes are mentioned in Section V. The gene localization method of the invention will be described with particular reference to FIG. 5, which shows in the upper portion of the figure, a region of chromosome which includes single-copy gene regions designated A, B, $C_0$, $C_1$, $C_2$, ... $C_n$, where A represents the region to be localized.

A cluster of junction-fragment probes designated $A/C_0$, $A/C_1$, $A/C_2$ and $A/C_n$ in FIG. 5 are produced in accordance with methods described above, such as the method illustrated in FIG. 4. The probes typically are cloned in a suitable vector, such as bacteriophage lambda. To hybridize the probes with the chromosome(s) of interest, the probe-containing cloning vectors, or suitable endonuclease digests thereof, are added to a cytoplasmic chromosome spread, and allowed to react with denatured chromosomal DNA under standard hybridization conditions. As seen in the lower portion of FIG. 5, in situ hybridization of the probes leads to probe binding to the A gene region and to each $C_i$ region for which an $A/C_i$ probe exists. The net effect is to hybridize a series of probes to a plurality of single-copy regions at and adjacent the A-region of interest.

To calculate an approximate number of probes available for binding to and adjacent the A region, it is assumed that, conservatively, at least half of the DNA sequences are unique, and that the average length of a probe end segment is about 2 kilobases. Thus, for a cluster of junction probes derived from DNA pieces roughly in the 20 to 500 kilobase size range, at least about 100 unique end segment probes capable of hybridizing in the locale of the A region will be formed. The number of probes, of course, can be easily increased by extending the range of sizes of DNA pieces from which the junction-fragment probes are derived. Thus the method can be practiced to bind at least about 100 probes to the DNA region to be localized.

The location of the junction-fragment probes on the chromosome can be detected by conventional methods, such as autoradiography or fluorescence microscopy. For autoradiographic determination, the junction-fragment probes are radiolabeled, preferably in their cloning vectors, by known techniques, such as nick-translation. After hybridizing the radiolabeled probes to the chromosomes, the chromosomal material is spread on autoradiography film, dried and exposed according to conventional techniques. Example XI below illustrates this autoradiography techniques for gene localization.

For detecting the hybridized probes by light or fluorescence microscopy, the junction-fragment probes in the probe cluster are preferably formed to include, at their junction regions, ligand marker segment by which a reporter-labeled anti-ligand can be attached to the probes. The reporter attached to the anti-ligand may include a variety of enzymes, chromophores or fluorescent reporter molecules. It is interesting to note that, in polytene phase chromosomes of Drosophila, fluorescent signal for detecting probe localization is achieved easily with a 1 kilobase probe. Assuming that there are a total of about 1,000 such probes bound to the polytene chromosome, and that the signal is sufficiently strong that the total number of probes could be reduced 5-fold and still achieve unambiguous localization of the probes, the method of the invention would provide a comparable microscopic visualization of a localized gene region with a cluster of about 100 probes, whose size average is about 2 kilobases.

VII. Forming a Bank of Genomic Probes

According to another application of the gene probe invention, there is provided a method for generating a series of junction-fragment probes derived from single-copy gene regions which are substantially uniformly spaced along a large portion of genomic DNA, which may include the entire genome. The gene region spacing may range between about 20 to 2,000 kilobases, depending on the intended application of the series of junction-fragment probes which are formed. As indicated above, one specific application of this method is in generating a series of probes which can be used to localize and identify single-copy polymorphic DNA regions which are associated with particular disease states. In this application, the probes are derived from gene regions which are preferably spaced about 1,000 kilobases from one another.

Figure 6:
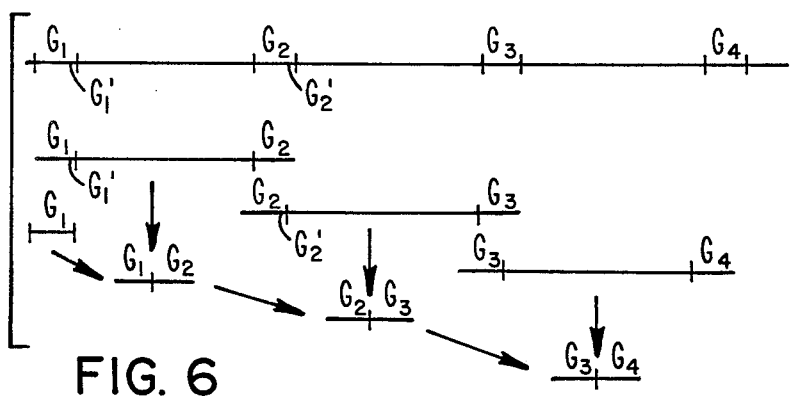
FIG. 6 illustrates a method for generating a series of gene probes derived from relatively evenly spaced single-copy regions of genomic DNA.

With reference to FIG. 6, there is shown a length of genomic DNA containing four single-copy gene regions, designated $G_1$, $G_2$, $G_3$ and $G_4$, which are spaced along the DNA strand at the desired-interval spacing. It is understood that the portion of DNA which is illustrated represents only a small portion of a single strand of DNA. The DNA is first digested to produce pieces like those shown in FIG. 6, whose end segments contain the adjacent gene regions of interest. The total DNA digest, which is typically a partial digest, may be size fractionated, according to methods described in Section II, to yield a DNA sample which is enriched in DNA pieces having a length corresponding approximately to the distance between adjacent $G_i$ genes. These pieces are circularized and digested to form junction fragments, including those designated $G_1/G_2$, $G_2/G_3$ and $G_3/G_4$ in FIG. 4.

Initially, the junction-probe fragments are selected, according to above-described methods (Section V) for the presence of a $G_1$ gene region and a second single-copy end segment, designated $G_2$ in FIG. 6. The orientation of $G_2$ with respect to $G_1$ can be ascertained by identifying, from a cloned insert of genomic DNA containing $G_1$, a short gene region $G_1'$ located immediately adjacent $G_1$, and a right-adjacent restriction endonuclease site, e.g., an EcoRI site, indicated in FIG. 6 by a vertical mark just to the right of $G_1'$. It can be appreciated from FIG. 6 that in all junction fragments containing both $G_1$ and $G_0$, the other probe end segment—i.e., $G_2$—will be derived from a gene region located to the right of $G_1$ in the figure, i.e., in the $G_1$-to-$G_1'$ direction. However, unless a circularized genomic-DNA end piece terminates in the region between the left end of the $G_1'$ region and the right-adjacent endonuclease site (a low probability occurrence due to the small size of this region), all junction probes which hybridize the $G_1$ probe, but not a $G_1'$ probe, will have a right-to-left segment orientation (opposite the $G_1$-to-$G_2$ orientation). Accordingly, by using the $G_1$ and adjacent $G_1'$ probes, $G_1/G_2$ junction probes having the desired $G_1$-to-$G_2$ orientation will be selected.

The newly selected $G_1/G_2$ probe is used to identify a junction fragment derived from the $G_2$–$G_3$ DNA piece which has yielded a $G_2/G_3$ junction fragment, as shown in the figure. This may be done by using the $G_1/G_2$ junction fragment to select, from a genomic DNA library of digest fragments of the genome, an insert containing $G_2$. From this insert, a $G_2'$ region to the right of the $G_2$ region and bounded by a right-adjacent endonuclease site can be identified (FIG. 6). All $G_2/G_3$ junction fragments which hybridize with both $G_2$ and $G_2'$ probes will then have the desired segment orientation, for the reason discussed above.

The selection procedure is repeated until junction-fragment probes, such as $G_3/G_4$, derived from gene regions spaced uniformly along the entire portion of the DNA of interest have been selected. The gene region or regions from which any of the probes were derived can be readily localized, by in situ hybridization, employing the general procedures described in Section VI above. Typically the location of every fifth to tenth junction fragment probe will be determined to confirm the positions of the gene regions from which the "intermediate" junction-fragment probes were derived.

To detect and localize DNA polymorphisms by the method of the invention, DNA derived from a sample of the population (e.g., 10–20 people) is treated with one of typically three restriction endonucleases whose recognition site is commonly associated with polymorphisms. These endonucleases include TaqI, MspI and HincII (reference 33). The digest DNA fragments are analyzed by Southern blot analysis and screened sequentially with the junction-fragment probes $G_i/G_{i+1}$. Restriction length fragment polymorphisms (RLFP) are evidenced by binding of a single radiolabeled probe to different bands (derived from different individuals) in the Southern blot. Procedurally, the fragments bound to the nitrocellulose filter in the Southern blot are exposed individually to one of the radiolabeled junction-fragment probes under hybridization conditions and the filter is then developed against X-ray sensitive film to detect the presence of bound probe. If variation in the band pattern for different individuals is not observed, a second probe in the series is similarly applied to the nitocellulose filter, which is again developed to detect the presence of bound probe. This procedure may be repeated five or six times with each filter.

Those probes which detect polymorphic regions of digested DNA may then be used to investigate the linkage between the identified polymorphic region and the associated inheritable disease gene.

In gene regions of particular interest, such as within the MHC system, which appear to contain a large number of polymorphisms linked to inheritable diseases, it may be advantageous to increase the resolution of the technique by forming a series of junction fragment probes derived from more closely spaced (e.g., 200 kilobases) gene regions.

VIII. Studying Gene Families

Figure 7:
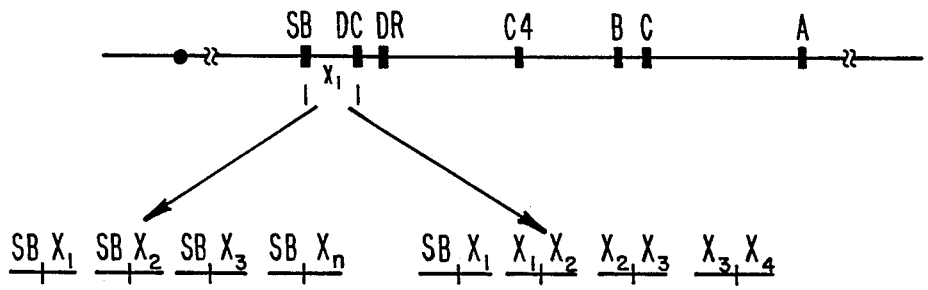
FIG. 7 indicates the derivation of junction-fragment probes useful for studying the SB/DC region of the MHC.

FIG. 7 is a map of the MHC, several gene regions of which are likely candidates for detailed study by the methods of the invention. One region of ihterest is the region of Class II gene between the SB and DR genes shown. This region, which may be up to 2 centimorgans in linkage distance, is believed to include several genes for heavy and light genes which have yet to be identified, and which may be found to correlate with disease states associated with a large number of known polymorphisms in this region (reference 16). As part of a systematic study of the region, it would be valuable to (1) determine the kilobase distance between the SB and DC genes and the DC and DR genes and (2) construct a cluster or series of junction fragment probes for identifying at least one cloned genomic digest insert every 50 to 100 kilobases within the region.

Probes derived from the SB, DC and DR gene regions have been reported (reference 35). To map the distance between the SB and DC gene regions, human genomic DNA containing these regions, and preferably derived from the above-described cell line which is hemizygous in chromosome 6 (reference 35a), is partially digested under conditions which produce predominantly 50 to 2,000 kilobase DNA pieces. Shorter-length partial digest pieces may be removed, for example, by centrifugation as described, and the remaining, predominantly large DNA pieces are then size fractionated, according to above methods, into a number of distinct size groups such as groups having size averages of about 50, 100, 200, 300, 400, 500 and greater than 500 kilobase pieces. Junction fragments produced from each of these size groups are screened successively with the SB, DC and DR probes to identify inserts containing two of the three gene regions. From the size of DNA pieces from which the identified junction fragments are derived, the approximate genomic-DNA distance between the corresponding two probe regions is known. For example, the distance between the SB and DC regions is approximately the length of DNA pieces from which was derived the junction fragment(s) capable of hybridizing both the SB and DC probes. Similar determinations of the DC to DR distance and the SB to DR distance would provide an internal check of the genomic distance determinations.

Junction fragment probes needed to identify genomic DNA digest inserts derived from the region of interest, such as the SB-DR region, can be constructed by either of two general methods which are discussed above. The first method involves forming a cluster of junction fragment probes, each of which has an end segment corresponding to one of the original probes, such as the SB or DR probes. The other end segment in each of the probes is derived from one of a plurality of single-copy regions located at increasing distances from the common end-segment region. FIG. 7 illustrates a cluster of probes, each having an SB probe end segment, and a second end segment derived from random single-copy gene regions located at various distances from the SB gene. The probes in the cluster are used to screen a genomic library, and will therefore identify all cloned inserts containing either the the SB gene or each region corresponding to one of the second end segments in the probe cluster. After the cloned inserts are identified, and assuming the entire region is represented by one or more of the inserts, a map of the region can be constructed by conventional overlap analysis of the inserts, in which single-copy end segments of one cloned insert are used to probe for corresponding internal regions of one or more overlapping inserts.

In a second method, illustrated generally at the right in FIG. 7, the SB-DR region of interest is subdivided into a number of substantially equal-distance intervals, according to the method described above with reference to FIG. 6, to produce a series of probes, such as those shown in FIG. 7, derived from substantially equally spaced intervals along the region. This cluster of probes is used to screen genomic DNA libraries, as above, to identify inserts containing one of the probe regions. The advantage of this method, obviously, is that since the approximate location of each of the junction-fragment probes is known, the work involved in constructing a map of the identified gene inserts is substantially reduced. Balanced against this is the greater effort needed to construct the series of probes by this sequential method.

The following examples illustrate various aspects of the invention, but are in no way intended to limit the scope thereof.

Bacterial Strains and Vectors

The following bacterial strains and vectors can be obtained from the American Type Culture Collections (ATCC), 12301 Parklawn Dr. Rockville, MD 20852; Bacterial strain LE392, (ATCC #33572); bacterial strain HB101 (ATCC #33694); and cosmid vector pHB8 (ATCC #37074). Bacterial strain CA0274 is available from the *E. coli* Genetic Stock Center, Dept. of Human Genetics, Yale School of Medicine, 333 Cedar St., New Haven, CT 30333, and is identified by stock #CGS 4990. Lambda phage Ch16A is available on rerquest from Dr. Fred Blattner, University of Wisconsin Laboratory of Genetics, 445 Henry Mall, Madison, WI 53706.

EXAMPLE I

Preparation of Genomic DNA Pieces

This example describes the preparation of genomic DNA digest pieces in the 35-45 kilobase size range. Peripheral blood lymphocytes were derived from normal individuals and the genomic DNA was isolated by successive phenol and phenol/chloroform (1:1) extractions, as described generally in reference 19. The DNA was suspended in a standard digest buffer to a concentration of about 0.5 micrograms/ml, and digested to completion with BamHI. The digest buffer included 150 mM NaCl, 6 mM MgCl$_2$, pH 7.9, and digestion was carried out for 60 minutes at 37° C. The BamHI was inactivated by heat treatment at 70° C. for 15 minutes. The digested DNA was extracted with phenol/chloroform, and precipitated with 70% ethanol.

The DNA digest pieces were size fractionated by ultracentrifugation, substantially as described in reference 36. Briefly, the DNA sample was heated for 10 minutes at 68° C., cooled to 20° C., then loaded on 10%–40% sucrose density gradients in ultracentrifugation tubes. The sucrose solution contained 100 mM NaCl, 10 mM Tris-HCl and 6 mM EDTA. The samples were centrifuged at 23,000 rpm, 14° C., for 20 hours.

To recover the fractionated DNA material, a small hole was punctured at the bottom of the centrifuge tube and successive 0.5 ml fractions were collected. These fractions were analyzed by agarose electrophoresis (0.3% agarose gel) using DNA fragments of known sizes as markers. The fractions identified as containing predominantly 35–45 kilobase pieces were combined and re-extracted with phenol, and phenol/chloroform and ethanol precipitated.

EXAMPLE II

This example describes the cloning of several of the BamHI digest pieces from Example I in a standard cosmid vector, and identification of the end segments in each of the cloned pieces. Cosmid vector pJB8, obtained from D. Ish-Horowicz (reference 37), was linearized by treatment with BamHI, and further treated with phosphatase, to prevent self-ligation. The linearized, phosphatase-treated cosmid (1 ug) was added to 1 ug of the BammHI digest pieces from Example I to a final DNA concentration of about 0.1 ug DNA per ul. Bacteriophage T4 DNA ligase (800 NEB units) was added, and the mixture was incubated overnight at 12° C. Conversion of the the DNA fragments to high-molecular-weight concatamers was confirmed by electrophoresis through a 0.4% agarose gel.

The ligated material was packaged using a standard lambda in vitro packaging system (reference 38), and the packaged material (0.25 ug DNA) was used to transfect the bacterial host E. coli strain HB101. Selection of bacterial hosts containing cosmid DNA was based on ampicillin resistance conferred on the host by an ampicillin resistance marker carried by the cosmid. Approximately 20 transfected colonies were selected, and the cosmid DNA was isolated from each colony by an alkaline lysis method, substantially as described in reference 37. The selected DNA preparations were resuspended in the above digest buffer. Each DNA preparation (1 ug) was mixed with BamHI (4 units) and the mixture was incubated at 37° C. for 30 minutes to release the BamHI inserts. The BamHI digest fragments were analyzed by electrophoresis through 0.7% agarose. Six of the selected cosmid vectors were identified as containing a single 35–45 kilobase BamHI insert. From each of the six selected vectors several hundred micrograms of vector DNA was prepared and treated with BamHI, to release the corresponding 35–45 kilobase insert. The BamHI digest fragments (100 ug) from each vector were fractionated by ultracentrifugation over a 10%–40% sucrose gradient, as in Example I, to obtain gradient fractions containing the 35–45 kilobase insert.

The insert pieces were radiolabeled at both ends by reacting the insert DNA with E. coli DNA polymerase, Klenow fragment, (5 units) in the presence of all four trinucleotides (2.5 mM), including $^{32}$P-labeled dGTP (reference 39). The labeled pieces were digested to completion with EcoRI, and the resultant EcoRI fragments were analyzed by electrophoresis on 0.8% agarose gel, followed by autoradiography, to identify the two BamHI/EcoRI end pieces in each of the cloned inserts. The BamHI/EcoRI end segments from cosmid B1-6 were identified as 2.2 and 2.4 kilobase gene regions which are shown, in the procedure described in Example III below, to be non-repetitive. The two BAM-HI/EcoRI end segments from cosmid B1-6 were subcloned into plasmid pBR328, which is widely available. The subcloned probes were nick-translated for use in several of the examples below.

EXAMPLE III

Selecting DNA Pieces Having Single-Copy End Segments

The end-labeled BamHI insert pieces from the six selected cosmid vectors in Example II, digested with EcoRI as described in Example II, were electrophoresed on 0.8% agarose gel and transferred to a nitrocellulose filters for Southern blot analysis (reference 40). The DNA fragments bound to the filter were hybridized with total blood lymphocyte DNA from Example I which had been radiolabeled by nick translation (reference 41). Single copy BamHI/coRI fragments were readily distinguished by autoradiography. Both the 2.2 and 2.4 kilobase BamHI/EcoRI end fragments from cosmid B1-6 were identified by this method as single-copy gene regions.

EXAMPLE IV

Circularization of DNA Pieces

The example describes the ligation of the 45 kilobase cosmid B1-6 insert (Example II) to form monomeric circles.

One ug of the 45 kilobase BamHI insert from cosmid B1-6, obtained as in Example II, was added to 30 to 1,500 microliters standard ligase buffer containing T4 DNA ligase (1.6 NEB units/microliter) to yield one of the four DNA concentrations, expressed in micrograms/microliter shown at the left in TABLE I below. These concentrations were selected on the basis of the ligation theory discussed above, which predicts that 45 kilobase fragments have an equal probability of forming either circles or linear concatemers at about a 10 micrograms/ml concentration. Ligation was carried out at 12° C. for 12 hours. After ligation, each of the DNA reaction mixtures was precipitated by the addition of 2 volumes of ethanol, and the precipitated DNA was resuspended in water to a final concentration of about 25 ug DNA/ml.

TABLE I

| [DNA] (ug/ml) | % circles |
|---|---|
| 0.6 | 96 |
| 1.25 | 75 |
| 3 | 60 |
| 30 | 15 |

To determine the percent of DNA comprising monomeric circles, each DNA fraction was digested to completion with EcoRI, under standard conditions. The EcoRI digest fragments (0.05 ug) were ligated into the EcoR site of-bacteriophage lambda Ch16A, which was then packaged, according to standard in vitro packaging procedures and plated on *E. coli* strain LE392, at a density of about 2,000 plaques per plate. The plaque DNA was fixed on nitrocellulose filters, substantially as described in reference 42, and these nitrocellulose filters were screened sequentially with the 2.2 and 2.4 BamHI/RI probe A described in Example II. If the 2.2 and 2.4 kilobase BamHI/EcoRI end pieces of the cosmid insert are denoted as A and B, respectively, it can be appreciated that ligation of the insert into monomeric circles will yield EcoRI fragments containing both A and B, whereas ligation into linear concatemers will yield end fragments which are 25% A ligated to A, 50% A ligated to B, and 25% B ligated to B. Thus, assuming substantially complete end-to-end ligation, the EcoRI fragments which hybridize the 2.2 kilobase (A) probe will consist of A-B fragments from monomeric circles plus A-A, A-B and B-B fragments from linear concatemers. Assuming that the B-B fragments represent one quarter of the fragments from linear concatemers, the percentage of original DNA molecules which form monomeric circles in the ligation reaction is thus calculated by (1) counting the number of plaques hybridizing with the A probe, (2) counting those which hybridize with the B probe only, and (3) applying the following equation:

$$\% \text{ circles} = \frac{\# \text{ of } A - 3 \text{ times } \# \text{ of } B \text{ only}}{\# \text{ of } A + \# \text{ of } B \text{ only}} \times 100$$

The results of this analysis are shown in TABLE I above. As seen, the percent monomeric circles increases from about 15%, at a reaction concentration of about 30 ug/ml, to about 95% at 0.6 ug/ml.

EXAMPLE V

Preparation of Suppressor tRNA Marker Segment

This example describes the preparation of a suppressor tRNA marker segment having BamHI ends. The segment is adapted for incorporation into the end-to-end junctions in circularized monomers of DNA pieces, as illustrated in Example VI below.

Plasmid pRD69 containing the gene for an amber suppressor tRNA was obtained on request from Dr. Robert Dunn at MIT. This is a pBR322 plasmid containing a synthetic tRNA which has been widely applied in the πVX cloning system (reference 32). The suppressor tRNA gene in the construct terminates at BamRI sites, and was obtained as an EcoRI fragment purified by electrophoresis on agarose gel. The purified suppressor gene, which was 207 base pairs in length, was blunt-ended by treatment with *E. coli* DNA polymerase, Klenow fragment, in the presence of all four deoxynucleotide triphosphates. BamHI linker having the sequence GGGATCCC, were obtained from Boehringer Mannheim. The linkers were ligated to the blunt ends of the suppressor gene substantially according to the procedure described in reference 43. The addition of the BamHI linkers, which begin with a G base, destroyed the EcoRI sites in the suppressor gene. The nucleotide sequence of the suppressor and attached BamHI linkers was confirmed by ligating a copy of the suppressor gene into the BamHI site of bacteriophage M13mp8 and determining the nucleotide sequence of the resulting phage by dideoxy sequencing (reference 44).

The suppressor gene was ligated into the BamHI site of pBR328 and the suppressor-containing plasmid was transfected into bacterial strain CARD-15 (obtained from Dr. Robert Dunn) which contains an amber mutated lac gene. Plating the transfected bacteria on MacConkey's agar, (Difco) containing lactose demonstrated that the suppressor gene retained its function. Approximately 1 mg of the plasmid was prepared, and the suppressor gene insert was obtained by BamHI digestion, followed by electrophoretic separation on 1.4% agarose, and electroelution.

EXAMPLE VI

Incorporation of Suppressor tRNA Into Monomeric Circles

This example describes the circularization of the cosmid B1-6 insert (Example II), in the presence of the suppressor tRNA gene fragment from Example V, to form circularized monomers containing one or more suppressor tRNA gene fragments at the end-to-end circle junction sites. Bacterial host *E. coli* strain CA274, which contains an amber-mutated lacZ gene and no suppressor genes of its own, was obtained from the Yale *E. Coli* Strain Repository. A second bacterial host, *E. coli* strain LE392, a suppressor positive strain, was obtained from N. Sternberg.

A reaction mixture including the purified cosmid insert, at a concentration of 0.8 ug/ml, the suppressor tRNA at a molar concentration roughly 500 times that of the DNA insert, and T4 DNA ligase, at a concentration of about 1.6 units per microliter was prepared in a standard ligase buffer. The mixture was incubated at 12° C. for 12 hours. Following ligation, the DNA was ethanol precipitated, resuspended in a standard ligase buffer, and digested to completion with EcoRI, releasing EcoRI junction fragments containing the two BamI/EcoRI end segments from the cosmid insert. The BamRI fragments were ligated into lambda Ch16A under standard conditions, followed by in vitro packaging, and plating on either bacterial host LE392 (the suppressor positive strain), or CA274. The phage DNA from the plates was fixed on nitrocellulose filters and screened with the above-designated A (2.2 kilobase segment) and B (2.4 kilobase segment) probes sequentially. The proportion of junction fragments which carried one or more suppressor genes in an A-B junction region was estimated by comparing the numbers of plaques which hybridized both A and B probes in the two host strains, after correcting for the difference in plaque-forming efficiency of the two hosts, based on the number of plaques appearing on each with a standard amount of lambda charon 28 phage. The results showed that approximately 20% of the A-to-B ligated DNA pieces have acquired at least one suppressor tRNA gene.

EXAMPLE VII

Incorporation of Biotinoylated Polynucleotide In Circularized Pieces

This example describes a method for incorporating a biotin-labeled polynucleotide marker segment into the junction region of circularized monomers of DNA pieces. A biotin-labeled polynucleotide segment is prepared as described in reference 26. Briefly, there is synthesized an analog of dTTP containing the biotin molecule covalently linked to the C-5 position of the pyrimidine ring through an allyl-amine link. A biotinoylated gene segment is formed from a short length of the filamentous bacteriophage M13, which has been copied in the presence of biotin-labeled dTTP, to form a biotin-labeled, double-stranded genome. Experimentally, M13 bacteriophage is copied by incubation with all four deoxynucleotides plus biotin-labeled dTTP which was present at a molar ratio of about 1:4 with respect to each of the other deoxynucleotides, in the presence of T4 DNA polymerase. After heat-inactivating the polymerase, the double-stranded bacteriophage is treated with a selected restriction endonuclease, such as HaeIII, which contains only C and G bases in its recognition sequence, and which therefore can act normally on double-stranded DNA containing biotin-labeled thymidine. The double-stranded material is digested to completion with the selected restriction endonuclease, under standard conditions, and small molecular weight pieces (preferably less than about 300 base pairs) are isolated by gel electrophoresis using 1.4% agarose gel. The fragments obtained are digested to completion with EcoRI and made blunt-ended by reaction with E. coli polymerase, Klenow fragment, in the presence of four deoxynucleotides as described in Example V. The SamHI linkers of Example V are attached to the fragment ends under conditions like those described in Example V. Fragments having sizes less than about 100 bases are removed electrophoretically. The resulting fragments contain biotin-labeled, double-stranded DNA having BamHI sites at their opposite ends.

The biotin-labeled fragments are incorporated into the junction-region of the 45 kilobase DNA fragments from Example I under conditions substantially like those described in Example VI. A reaction mixture containing about 0.6 ug/ml of the DNA insert pieces and an approximately 500-fold molar excess of the biotin-labeled pieces are incubated in the presence of T4 ligase at about 12° C. for 12 hours, after which the circularized DNA pieces are isolated by ethanol precipitation. The precipitated circularized monomers are resuspended in a suitable digest buffer and digested to completion with EcoRI, also as described in above Example VI, to produce junction fragments containing the A and B gene segment joined at a junction region by one or more short biotin-labeled segments.

The biotin-labeled junction fragments are separated from the other EcoI digest fragments by affinity chromatography using antibody-sepharose, prepared by coupling anti-biotin antibody to cyanogen bromide-activated sepharose 4B, as described in reference 45. Columns containing the resin are equilibrated with a suitable buffer, such as 10 mM Tris HCl, pH 7.5 and the DNA samples are applied to the column in the same buffer, then washed with several volumes of the same buffer. These conditions are effective to bind substantially all of the biotin-labeled BamRI fragments to the column. The bound biotin-labeled fragments are eluted from the column with 6 M urea/1M NaCl. Alternatively biotin-labeled fragments could be bound by antibiotin antibody and purified over a column of Staphylococcus aureas protein A as described in references 26 and 29.

EXAMPLE VIII

Preparing a Heterogeneous-Size Cluster of Junction Probes

The examples above are concerned with the construction of a junction probe derived from a cloned 45 kilobase insert. The present example, and following Examples IX and X, describe the preparation of a cluster of junction probes prepared from heterogeneous-size genomic DNA fragments. Each probe in the cluster is selected to include one end segment which has a first segment which hybridizes to probe A, and a second segment derived from a single-copy region which in the genomic DNA, is located at one of a number of different spacings in the 40–1,000 kilobase range, from the probe A region.

Genomic DNA is obtained from peripheral blood lymphocytes, according to Example I, and the DNA strands are partially digested with Sau3A, under conditions which produce a significant portion of DNA fragments in the 40 to 1000 kilobase size range. The desired size distribution of partial digest fragments can be varied readily by controlling the length of the digestion reaction. The partial digest of genomic DNA is fractionated, preferably by ultracentrifugation on a 10%–40% sucrose gradient according to methods described in Example I, and DNA fractions containing sizes of greater than about 40 kilobases, as determined by agarose gel electrophoresis, are separated from smaller DNA pieces and pooled.

A circularization reaction mixture containing the large DNA pieces, at a concentration of about 0.15 ug/ml, and an approximately 500-fold molar excess of the suppressor tRNA segment prepared as in Example V, is incubated in the presence of T4 DNA ligase (1.6 units per microliter) at 12° C. for 24 hours, to produce monomeric circularization of a major portion of the DNA pieces. The reaction is terminated by chilling, and the DNA precipitated by ethanol.

The circularized DNA is digested to completion with EcoRI, under standard conditions, to release EcoRI junction fragments, a portion of which will include one or more of the suppressor tRNA markers incorporated into the junction site. The EcoRI fragments are ligated into lambda Ch16A, as described in Example VI, and the insert-containing lambda phage is packaged and plated on E. coli strain CA274 also as described in Example VI. Plaque DNA is transferred to nitrocellulose filters, fixed on the filters, and then screened with the radiolabeled probe A. The regions of filters showing radioactivity correspond to plaques which are transfected with phage containing a junction fragment insert having a suppressor tRNA junction segment, and a single-copy segment complementary to probe A.

Lambda phage DNA from each of the plaques identified as a junction fragment capable of hybridizing to the probe A was extracted, digested to completion with EcoRI, and analyzed by Southern blotting for the presence of multiple-copy DNA segments in the junction probe. Southern blot analysis was performed according to standard procedures, with the fractionated EcoRI fragments being analyzed by radiolabeled probe A, to identify the junction probe insert, and followed by a second hybridization with nick-translated total genomic DNA from peripheral lymphocytes to identify those junction probes containing multiple-copy segments. Plaques containing multiple-copy segments in the junction probe are either subjected to subcloning or discarded. The remaining plaques provide a cluster of junction probes, each containing a probe A segment and, attached thereto through one or more tRNA segments, another single-copy segment which is separated from the probe A region by a variable spacing which may range between about 40 kilobases and up to 1000 kilobases or greater, depending on the largest sizes of the original partial-digest DNA pieces.

EXAMPLE IX

Preparation of a Cluster of Junction Probes Having Selected Gene Segment Spacings-Method 1

The present example illustrates a method for generating a cluster of probes, each of which contains a first probe A segment and a second segment derived from a gene region having a selected spacing, in the genome, from the probe-A region. Genomic DNA obtained from peripheral lymphocytes, as in Example I, is partially digested, as in Example VIII, to yield DNA pieces which are substantially in the 40 to 1,000 kilobase size range. The DNA pieces are fractionated by ultracentrifugation on a sucrose gradient, according to known methods, and 0.5 ml fraction obtained by dripping the gradients into sample tubes are each analyzed by electrophoresis on 0.2% agarose, according to standard procedures (references 21 and 22). Samples identified as containing DNA fragments which are distributed substantially in the 50, 100, 200, 500 and 500+ kilobase size ranges, are selected.

Each of the five size-selected samples of DNA pieces is ligated in the presence of an approximately 500-fold molar excess of suppressor tRNA, under conditions which lead to predominantly monomeric circle ligation. As indicated in Example IV, the concentration of DNA pieces required to produce substantially complete circular monomerization for DNA pieces in the 45 kilobase size range is about 0.6 micrograms/ml. This concentration is selected for the ligation of the DNA pieces having average sizes of about 50 kilobases, as indicated in TABLE II. The DNA concentrations of the four larger size distributions of DNA pieces are reduced in proportion to the square root of the average kilobase size of the pieces, in accordance with the above-discussed theory, and as indicated in the right-hand column in TABLE II. Each of the reactions is carried out in the presence of T4 ligase, at a concentration of 1.6 units per microliter at 14° C. for 24 hours. After terminating the reaction by cooling, the circularized DNA pieces from each of the five reactions is extracted successively with chloroform and ethanol and resuspended in a suitable digest buffer.

The ligated DNA fractions are digested to completion with EcoRI, producing, in each size group, a portion of junction fragments containing one or more suppressor tRNA segments at the junction site. In each size group, the complete-digest EcoRI fragments are ligated into lambda Ch16A phage, as described in Example VI, followed by in vitro packaging of the phage DNA and plating on the suppressor-deficient *E. coli* strain CA274, also in accordance with the method of Example VI. Those plaques which are identified by this method were selected, forming, for each of the five size groups, a library of junction-probe inserts containing single-copy DNA segments which are separated, in the genomic gene, by an average of either 50, 100, 200, 500 or 1,000 or more kilobases.

TABLE II

| average size (kilobase) | [DNA] (ug/ml) |
| --- | --- |
| 50 | 0.6 |
| 100 | 0.4 |
| 200 | 0.3 |
| 500 | 0.2 |

TABLE II-continued

| average size (kilobase) | [DNA] (ug/ml) |
| --- | --- |
| 500+ | 0.1 |

Each of the five libraries is screened for junction-fragment inserts containing the gene segment complementary to probe A, by hybridizing the nick-translated probe A with the plaque DNA on nitrocellulose filter and may be further selected for single-copy gene regions in the junction probes, using nick-translated total genomic DNA fragments as probes. The selected plaques in each group now contain a plaque lambda insert composed of a first segment, complementary to probe A, a suppressor tRNA segment, and a second single-copy segment derived from a gene region whose spacing from the probe A region in genomic DNA is slightly less than the size of DNA piece from which the insert was derived.

EXAMPLE X

Preparation of a Cluster of Junction Probes Having a Selected Gene-Segment Spacing-Method 2

This example describes a second method for preparing a cluster of junction probes, derived from size-distributed DNA pieces. In the method, peripheral lymphocyte genomic DNA is partially digested, as in above examples VIII and IX, to form digest fragments predominantly in the 40 to 1000 kilobase size range. The material is partially purified by ultracentrifugation on a 10%–40% sucrose gradient, as described in Example I, to remove DNA pieces having average sizes less than about 40 kilobases. The preparation of large partial-digest pieces is divided into five equal-volume aliquots and each sample is diluted to concentration of about 0.15 ug/ml in a suitable ligation buffer also containing T4 ligase at a concentration of about 1.6 units per ul. The ligation reaction in each sample is carried out at 12° C. Initially, a 500 fold molar excess of the suppressor tRNA segment from Example V is added to one of the samples, which is then allowed to react at for an additional 15–60 minutes, leading to the incorporation of one or more suppressor tRNA segments into circularized DNA pieces whose sizes are skewed toward the smaller DNA pieces by virtue of the relatively more rapid circularization which occurs in the smaller pieces in the reaction mixture. After the first reaction period, the sample containing the added suppressor tRNA is cooled to terminate the reaction, and the DNA is successively extracted with chloroform and ethanol, as described above. Also after the first 15–60 minute reaction period, a 500-fold molar excess of suppressor tRNA is added to a second reaction mixture, and the circularization reaction in the presence of the suppressor tRNA is allowed to continue an additional 30–120 minute time period, leading to the production of circularized monomers, a portion of which contain one or more suppressor tRNA segments at their junction sites. The size distribution of circles incorporating suppressor tRNA segment(s) will be somewhat larger than that of the first reaction mixture since the smallest fragments will circularize before the suppressor tRNA is added and larger fragments will circularize in the second reaction period. The reaction in the second mixture is terminated, after the 30–120 minute reaction period, as above, at which time a 500-fold molar excess of suppressor tRNA is added to a third reaction mixture which is also allowed to react an additional 30–180 minutes, leading to incorporation of the suppressor tRNA into circles having a still larger size distribution. Similarly, suppressor tRNA is added to the fourth and fifth reaction mixtures at progressively longer times after the initial ligation reaction is begun, after which the reaction mixture is incubated an additional 1–3 or 2–6 hours, respectively, at 12° C.

The five DNA mixtures, which differ in the size distribution of circularized monomers containing one or more suppressor tRNA's at the junction site, are digested to completion with EcoRI, and the total-digest fragments are ligated into lambda Ch16A, which is then packaged and used to transfect suppressor-negative $E.$ $coli$ strain CA274, allowing selection for phage carrying a suppressor insert. Plaques which are identified, by nitrocellulose filter hybridization, to hybridize with nick-translated probe A from Example II, and which do not contain a multiple-copy gene segment, as determined by nitrocellulose filter hybridization with nick-translated total genomic DNA, are selected, forming for each of the different size-distribution classes, a library of phage clones containing junction fragments composed of the probe A segment joined by one or more suppressor tRNA segments to a single-copy segment of the gene.

EXAMPLE XI

Localization of the Probe a Gene Region

Peripheral blood lymphocytes are grown in a standard cell culture (reference 46). Colchicine is added to the culture, to arrest the cells in metaphase, and the cells are treated to produce a cytoplasmic spread of the chromosomes, by standard procedures (reference 46). The chromosomal DNA is heat denatured, according to known procedures (reference 46). The plaques of phage lambda selected in Example VIII to contain junction fragment inserts composed of a single-copy gene region joined through one or more suppressor tRNA's to a gene segment which is complementary to probe A, are radiolabeled by nick translation. The radiolabeled phage DNA is added to the cytoplasmic chromosome spread and allowed to react with the denatured chromosomal DNA under hybridization conditions. The chromosomal material is spread on autoradiography film, dried, and the film is exposed for a period of 7 days. The film label shows a concentration of radioactive label on a localized region of one of the chromosomes only, thereby identifying this region as the site of the single-copy DNA segment corresponding to the probe A.

From the foregoing, it can be appreciated how the present invention provides the several important objects and advantages noted above. Where probes corresponding to two gene regions are available, the method of the invention can be practiced to determine the distance between and/or orientation of the two genomic gene regions. Where a single probe corresponding to a single-copy region of the gene is available, the invention provides a method for localizing the probe gene region by hybridization (Section VI) and for studying the identity and positions of genes or gene families which lie within a distance of up to several thousand kilobases of the known gene region (Section VIII).

The invention also provides a unique method for generating a family of probes derived from relatively evenly spaced single-copy gene regions along a genomic DNA, as a tool for identifying DNA polymorphisms associated with inheritable disease states, as part of a systematic study which can ultimately lead to the localization and identification of disease-producing genes.

While preferred embodiments of the invention have been described, it will be appreciated that various changes and modifications can be made without departing from the spirit of the invention.

What is claimed is:

1. A method of forming a probe capable of binding by homologous base pairing independently to an upstream gene region which is present on a linear section of mammalian genomic DNA and which binds by homologous base pairing to a selected probe, and to a downstream gene region which is also present on said section and is spaced from the upstream gene region by a distance of about 20–2,000 kilobases, said method comprising
   digesting the mammalian genomic DNA section by endonuclease treatment to produce genomic fragments, at least some of which have sizes consistent with section fragments containing said upstream and downstream regions at their opposite ends,
   ligating the genomic fragments under fragment concentration conditions which favor circularization of single fragments into circular DNA species with connected fragment ends,
   digesting the circular DNA species by endonuclease treatment to release digest fragments which are of a size which can be cloned, and which include fragments containing such connected fragment ends,
   cloning the digest fragments, and
   isolating cloned digest fragments which contain the connected fragment ends, and which are able to bind by homologous base pairing to the selected probe.

2. The method of claim 1, for producing a probe capable of binding by homologous base pairing to such upstream and downstream gene regions, where such are separated by a selected distance between about 20 and 2,000 kilobases, which further includes, prior to said ligating, size fractionating the genomic fragments and selecting for ligating, those fragments having sizes corresponding to the selected distance between the two gene regions.

3. The method of claim 1, for producing a second probe capable of binding independently to the downstream gene region and to a third gene region present on the linear DNA section, which is spaced from and downstream fo the downstream gene region by a distance between about 20 and 2,000 kilobases, which further includes isolating cloned digest fragments which contain the connected fragment ends, and which are able to bind by homologous base pairing to the probe isolated by the first isolating step, but not to such selected probe.

4. The method of claim 1, for producing a cluster of probes, all of which are capable of binding independently by homologous base pairing to such upstream gene region, and each of which is capable of binding by homologous base pairing to one of a series of such downstream regions which are separated from the upstream gene region by different distances between about 20 and 2,000 kilobases, wherein said digesting is carried out under conditions which produce fragments having heterogeneous sizes greater than about 20 kilobases.

5. The method of claim 4, for use in localizing such upstream gene region on the linear DNA strand, which further includes labeling the cluster of probes with a reporter, hybridizing the cluster of labelled probes with the linear DNA strand, and identifying the region of DNA section having bound reporter.

6. The method of claim 1, which further cleaving the isolated digest fragments which contain the connected fragment ends, and which are able to bind by homologous base pairing to the selected probe, to release digest fragment portions which are able to bind by homologous base pairing to the downstream, but not the upstream gene region of the DNA section.

7. The method of claim 1, wherein said ligating is performed within a concentration range of genomic fragments which is substantially inversely proportional to the square root of the sizes of the fragment where the ligating is performed in a concentration range of between about 0.5 to 1.0 micrograms fragment DNA per ml for fragments in the approximately 50 kilobase size range.

8. The method of claim 1, which further includes, prior to said ligating, attaching to the DNA genomic fragments, a selectable marker by which a released digest fragment containing such marker can be selected in a cloning system.

9. The method of claim 8, wherein the marker includes a suppressor tRNA gene, for selection in a cloning system which includes a phage vector carrying such fragment, and a bacterial vector host which is suppressor-tRNA negative.

10. The method of claim 1, which further includes, prior to said ligating, attaching to the DNA genomic fragments, a ligand marker segment by which a released monomer fragment containing the marker segment can be isolated by binding to an anti-ligand, prior to said cloning.

11. The method of claim 1, wherein the ligand marker is a biotinylated DNA segment, and the anti-ligand is avidin or anti-biotin antibody.

12. A probe comprising
a first DNA segment (1) derived from the upstream end region of a linear fragment of mammalian genomic DNA having upstream and downstream end regions which are spaced from one another by between about 20-2,000 kilobase and (2) which is effective to bind by homologous base pairing to said upstream end region in genomic DNA, and
a second DNA segment (1) derived from the downstream end region of said DNA fragment and connected adjacent its downstream end, as defined by the upstream-to-downstream orientation in the DNA fragment, to the upstream end of the first segment, and (2) which is effective to bind by homologous base pairing to said downstream and region in genomic DNA,
where the total length of the probe is substantially less than that of said DNA fragment, and of a size which can be cloned.

13. The probe of claim 1, wherein the first and second segments are joined through an intermediate segment which is not derived from said DNA fragment.

14. The probe of claim 13, wherein the intermediate segment is a selectable marker segment which allows probe selection in a cloning system.

15. The probe of claim 14, wherein the selectable marker segment is a suppressor tRNA which allows for selection of a phage vector containing the probe in a suppressor (−) host.

16. The probe of claim 13, wherein the intermediate segment is a ligand adapted to bind specifically and with high affinity to an anti-ligand.

17. The probe of claim 16, wherein the ligand is biotin, and the anti-ligand is avidin or anti-biotin antibody.

18. The probe of claim 12, for use in binding to upstream and downstream gene regions which are spaced a seelcted distance from one another in the DNA section, wherein the DNA fragment from which said first and second segments are derived has a length substantially equal to such selected distance.

19. The probe of claim 12, wherein the upstream and downstream gene regions in the DNA fragment are each single-copy regions.

20. The probe of claim 12, wherein said first and second segments are connected by direct ligation to one another.

21. A cluster of probes each comprising
a first DNA segment (1) derived from the upstream end region of one in a group of fragments of mammalian genomic DNA, where each fragment in the group has upstream and downstream end regions which are spaced from one another by between about 20-2,00 kilobases, and where the fragments in the group have the same upstream end region and different downstream end regions, and (2) which is effective to bind by homologous base pairing to said one fragment's upstream end region in genomic DNA, and
a second DNA segment (1) derived from the downstream end region of said one DNA fragment and connected adjacent its downstream end, as defined by the upstream-to-downstream orientation in the DNA fragment, to the upstream end of the first segment, and (2) which is effective to bind by homologous base pairing to said one fragment's downstream end region in genomic DNA,
where the total length of the probe is substantially less than that of said one DNA fragment, and of a size which can be cloned.

22. The cluster of claim 21, wherein the second segment in each probe is derived from a single-copy gene of said DNA fragment.

23. A cluster of probes each comprising
a first DNA segment (1) derived from the upstream end region of one in a group of fragments of mammalian genomic DNA, where each fragment in the group has upstream and downstream end regions which are spaced from one another by between about 20-2,000 kilobases, and where the downstream end region of one fragment in the group is essentially the same as the upstream end region of another fragment in the group, and (2) which is effective to bind by homologous base pairing to said one fragment's upstream end region in genomic DNA, and
a second DNA segment (1) derived from the downstream end region of said one DNA fragment and connected adjacent its downstream end, as defined by the upstream-to-downstream orientation in the DNA fragment, to the upstream end of the first segment, and (2) which is effective to bind by homologous base pairing to said one fragment's downstream end region in genomic DNA,
where the total length of the probe is substantially less than that of said one DNA fragment, and of a size which can be cloned.

24. The cluster of claim 23, wherein the first and second segments in each probe are joined through an intermediate segment which is not derived from the DNA fragment.

* * * * *

UNITED STATES PATENT AND TRADEMARK OFFICE
CERTIFICATE OF CORRECTION

PATENT NO. : 4,710,465

DATED : Dec 1, 1987

INVENTOR(S) : Sherman M. Weissman & Francis Collins

It is certified that error appears in the above-identified patent and that said Letters Patent is hereby corrected as shown below:

Column 6, line 11, after "a novel probe" insert --comprising a first segment which is derived from a first gene region of a fragment of DNA, and a second segment which is derived from a second gene region which is positioned downstream of and spaced from the first gene region of the DNA fragment between about 20-2,000 kilobases. The upstream end of the first segment--.

Column 22, line 53, change "requrest" to --request--.

In the claims:

Column 34, line 23, change "20-2,00" to --20-2,000--.

Signed and Sealed this

Twenty-seventh Day of February, 1990

Attest:

JEFFREY M. SAMUELS

Attesting Officer       Acting Commissioner of Patents and Trademarks